US012586684B2

(12) United States Patent
Chaudhuri et al.

(10) Patent No.: US 12,586,684 B2
(45) Date of Patent: Mar. 24, 2026

(54) DECISION SUPPORT TOOLS FOR REDUCING READMISSIONS OF INDIVIDUALS WITH ACUTE MYOCARDIAL INFARCTION

(71) Applicant: CERNER INNOVATION, INC., Kansas City, KS (US)

(72) Inventors: Rupanjali Chaudhuri, Bangalore (IN); Vadim Khotilovich, Leawood, KS (US); Monica Gaur, Delhi (IN); Chetan KV, Bangalore (IN); Will Zimmerman, Kansas City, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 253 days.

(21) Appl. No.: 17/646,578

(22) Filed: Dec. 30, 2021

(65) Prior Publication Data

US 2023/0215563 A1 Jul. 6, 2023

(51) Int. Cl.
*G16H 50/20* (2018.01)
*G16H 10/60* (2018.01)
*G16H 50/30* (2018.01)

(52) U.S. Cl.
CPC ............. *G16H 50/20* (2018.01); *G16H 10/60* (2018.01); *G16H 50/30* (2018.01)

(58) Field of Classification Search
CPC ........ G16H 50/30; G16H 10/60; G16H 50/20; G16H 40/20; G16H 50/50; G16H 20/10; G16H 20/30
See application file for complete search history.

(56) References Cited

U.S. PATENT DOCUMENTS 8,949,082 B2 * 2/2015 Farooq ................... G16H 50/70
703/2
10,943,676 B2 * 3/2021 Farooq ................... G16H 50/70
(Continued)

FOREIGN PATENT DOCUMENTS

WO WO-9748327 A1 * 12/1997 ......... G01N 33/6887

OTHER PUBLICATIONS

Tran, Kaleen Elizabeth. Evaluation of the Use of a Remote Care Platform to Reduce 30-Day Readmission Rates for Post-Acute Myocardial Infarction Patients. Thesis for the University of Louisiana at Lafayette. Spring 2020. (Year: 2020).*
(Continued)

*Primary Examiner* — Christopher L Gilligan
*Assistant Examiner* — Tristan Isaac Evans
(74) *Attorney, Agent, or Firm* — Invoke

(57) ABSTRACT

System, methods and computer storage media are disclosed for providing a decision support tool for reducing readmissions of AMI patients through early prediction of readmission. An AMI patient may be identified using a working diagnosis and/or an elevated troponin level. One or more machine learning models may be utilized to predict readmission at a time prior to discharge. Based on the prediction, an intervening action may be automatically initiated. Further embodiments include training machine learning model(s) to predict readmission of an AMI patient. In some embodiments, a first model may be trained using reference patient data as it existed at a predetermined time following the patient's admission (e.g., 12 hours after admission), and a second model may be trained using reference patient data as it existed at a later time (e.g., discharge). Readmission risk scores from each model may be combined to determine an overall risk for an AMI patient.

28 Claims, 13 Drawing Sheets

(56) References Cited

U.S. PATENT DOCUMENTS

| | | | | |
|---|---|---|---|---|
| 11,355,240 | B2* | 6/2022 | Hirsch | G16H 50/20 |
| 11,610,679 | B1* | 3/2023 | Zhan | G06N 3/096 |
| 2012/0046965 | A1* | 2/2012 | Ryan | G16Z 99/00 |
| | | | | 705/2 |
| 2015/0213225 | A1* | 7/2015 | Amarasingham | G16H 50/30 |
| | | | | 705/2 |
| 2016/0188814 | A1* | 6/2016 | Raghavan | G06N 5/04 |
| | | | | 705/2 |
| 2017/0109494 | A1* | 4/2017 | Nunez | G16H 40/63 |
| 2018/0330826 | A1* | 11/2018 | Wan | G16H 50/20 |
| 2021/0193327 | A1* | 6/2021 | Sankar | G06F 17/18 |
| 2021/0241871 | A1* | 8/2021 | Burnett | G16H 70/60 |
| 2023/0105348 | A1* | 4/2023 | Vodencarevic | G16H 10/60 |
| | | | | 705/2 |
| 2025/0087361 | A1* | 3/2025 | Sutton | G16H 10/60 |

OTHER PUBLICATIONS

Lo. Predictive modeling for 14-day unplanned hospital readmission risk by using machine learning algorithms. BMC Medical Informatics and Decision Making 2021, 21(1):288 (Oct. 2021). (Year: 2021).*

Smith. Acute Myocardial Infarction Readmission Risk Prediction Models. Circ Cardiovasc Qual Outcomes. 2018; 11:e003885. DOI: 10.1161/CIRCOUTCOMES.117.003885. (Year: 2018).*

Rojas. Predicting Intensive Care Unit Readmission with Machine Learning Using Electronic Health Record Data. Ann Am Thorac Soc vol. 15, No. 7, pp. 846-853, Jul. 2018. This paper speaks directly about the use of machine learning in readmission prediction. (Year: 2018).*

Nguyen et al. Predicting 30 Day Hospital Readmissions in Acute Myocardial Infarction: The AMI "READMITS" (Renal Function, Elevated Brain Natriuretic Peptide . . . Journal of the American Heart Association, vol. 7, Issue 8, Apr. 2018 https://doi.org/10.1161/JAHA.118.008882. (Year: 2018).*

Hebert, C., Shivade, C., Foraker, R et al. Diagnosis-specific readmission risk prediction using electronic health data: a retrospective cohort study. BMC Med Inform Decis Mak 14, 65 (2014). https://doi.org/10.1186/1472-6947-14-65 (Year: 2014).*

Du, Guodong, et al. "Prediction of 30-day readmission: an improved gradient boosting decision tree approach." Journal of Medical Imaging and Health Informatics 9.3 (2019): 620-627. (Year: 2019).*

Yuan Xu, et al. Extreme Gradient Boosting Model Has a Better Performance in Predicting the Risk of 90-Day Readmissions in Patients with Ischaemic Stroke, Journal of Stroke and Cerebrovascular Diseases, vol. 28, Issue 12, 2019, 104442, ISSN 1052-3057. (Year: 2019).*

Kakarmath et al. Validating a Machine Learning Algorithm to Predict 30-Day Re-Admissions in Patients With Heart Failure: Protocol for a Prospective Cohort Study JMIR Res Protoc 2018;7(9):e176. (Year: 2018).*

Awan SE et al. (2019) Feature selection and transformation by machine learning reduce variable numbers and improve prediction for heart failure readmission or death. PLoS ONE 14(6): e0218760. (Year: 2019).*

Philbin et al. "Prediction of Hospital Readmission for Heart Failure: Development of a Simple Risk Score Based on Administrative Data" Journal of the American College of Cardiology vol. 33, No. 6, 1999. (Year: 1999).*

N. L. Fitriyani, M. Syafrudin, G. Alfian and J. Rhee, "HDPM: An Effective Heart Disease Prediction Model for a Clinical Decision Support System," in IEEE Access, vol. 8, pp. 133034-133050, 2020. (Year: 2020).*

Hashi, E. K., & Md. Shahid Uz Zaman. (2020). Developing a Hyperparameter Tuning Based Machine Learning Approach of Heart Disease Prediction. Journal of Applied Science Process Engineering, 7(2), 631-647. (Year: 2020).*

P. Anuradha and V. K. David, "Feature Selection and Prediction of Heart diseases using Gradient Boosting Algorithms," 2021 International Conference on Artificial Intelligence and Smart Systems (ICAIS), Coimbatore, India, Mar. 25, 2021, pp. 711-717. (Year: 2021).*

* cited by examiner

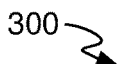
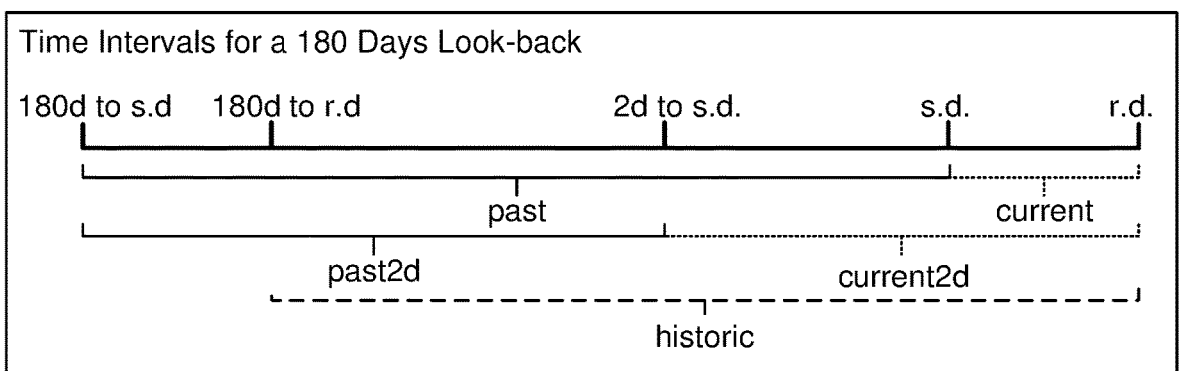
*FIG. 3.*

400

| Admit Features | Admit Coefficients |
|---|---|
| latest_ccs_cci_5_mental_clin_valid_current_any_conditions | -0.412189998 |
| count_emergency_visit_enc_past_encounters_180_days | 0.170838131 |
| min_hgb_obstype_current_numeric_results | -0.001962774 |
| latest_tobacco_user_clin_valid_current_any_conditions | 0.230271089 |
| age_in_years | 0.005508538 |
| latest_combined_bnp_current_numeric_results | 0.103167226 |
| max_combined_bnp_past_numeric_results_365_days | 0.093818573 |
| latest_insulin_med_valid_historic_medications | 0.140969109 |
| enc_ref_inp1 | 0.139867305 |
| max_pain_score_current_numeric_results | 0.017516016 |
| min_albumin_obstype_current_numeric_results | -0.014736127 |
| count_emergency_visit_enc_past_encounters_365_days | 0.07997213 |
| count_emergency_visit_enc_past_encounters_730_days | 0.07187112 |
| min_chloride_level_obstype_historic_numeric_results_90_days | -0.016189087 |
| unknown_instype_insurance_coverage | -0.102209407 |
| min_sodium_level_obstype_past_numeric_results_365_days | -0.012287834 |
| max_bun_obstype_historic_numeric_results_730_days | 0.123491373 |
| count_left_ama_dcdis_past_encounters_730_days | 0.171484573 |
| count_observation_visit_enc_past_encounters_730_days | 0.059879471 |
| earliest_troponin_obstype_current_numeric_results | 0.157184033 |
| latest_loop_diuretics_group_valid_administrator_dispenser_current_medications | 0.086404211 |
| gender_demographics_male | 0.072126047 |
| latest_ccs_cci_3_endocrine_nutritional_metabolic_immunity_clin_valid_current_any_conditions | -0.072823221 |
| max_potassium_level_obstype_historic_numeric_results_90_days | 0.059154755 |
| latest_chronic_kidney_disease_clin_valid_current_any_conditions | 0.06813994 |
| latest_liver_disease_moderate_or_severe_clin_valid_current_any_conditions | 0.307787642 |
| earliest_combined_bnp_current_numeric_results | 0.037404794 |
| commercial_instype_insurance_coverage | -0.058747894 |
| latest_morphine_valid_current_medications | 0.058126272 |
| median_albumin_obstype_current_numeric_results | -0.008977787 |
| latest_hydromorphone_med_valid_administrator_dispenser_current_medications | 0.113309455 |
| latest_ccs_cci_7_circulatory_clin_valid_historic_any_conditions | 0.051037575 |
| latest_ccs_cci_7_circulatory_clin_valid_current_any_conditions | -0.066293709 |
| max_serum_magnesium_obstype_past_numeric_results_90_days | 0.08488396 |
| max_bun_obstype_past_numeric_results_90_days | 0.06849071 |
| latest_liver_disease_moderate_or_severe_clin_valid_past_any_conditions | 0.243109102 |
| latest_ccs_cci_2_neoplasms_clin_valid_historic_any_conditions | -0.10998408 |
| latest_spironolactone_oral_med_valid_historic_medications | 0.058922685 |
| latest_ccs_cci_6_nervous_and_sense_clin_valid_current_any_conditions | -0.043271407 |
| count_inpatient_visit_enc_past_encounters_180_days | 0.033406215 |
| median_pain_score_past_numeric_results_90_days | 0.009408786 |
| latest_ccs_cci_12_skin_and_subcutaneous_clin_valid_current_any_conditions | 0.09691713 |
| latest_myocardial_infarction_clin_valid_current_any_conditions | 0.039059576 |
| bin_max_inr_obstype_past_numeric_results_180_days | 0.057198503 |
| min_sodium_level_obstype_current_numeric_results | -0.005004527 |
| min_pulse_oximetry_obstype_past_numeric_results_90_days | -0.004469185 |
| latest_transplant_proc_past_procedures | -0.406658519 |
| max_glucose_obstype_past_numeric_results_90_days | 0.075765484 |
| latest_antibiotic_misc_pharmacotherapy_med_valid_historic_medications | 0.056682945 |
| earliest_encounter_types_inpatient_current_encounters | 0.026523755 |
| latest_valvular_heart_disease_clin_valid_current_any_conditions | 0.030845847 |
| latest_coagulation_disorder_clin_valid_current_any_conditions | 0.032300279 |
| latest_cardiac_arrhythmia_clin_valid_current_any_conditions | 0.015735147 |
| latest_pneumonia_valid_past_any_conditions | 0.019451352 |
| min_chloride_level_obstype_historic_numeric_results_730_days | -0.00141782 |
| latest_cardiac_cath_and_angiography_proc_past_procedures | 0.011475801 |
| latest_ccs_cci_10_genitourinary_clin_valid_current_any_conditions | 0.009263877 |
| max_platelet_count_obstype_current_numeric_results | 0.03875684 |
| latest_hypertension_clin_valid_current_any_conditions | -0.005205592 |

| Discharge Features | Discharge Coefficients |
|---|---|
| latest_ccs_cci_5_mental_clin_valid_current_any_conditions | -0.451357725 |
| max_bun_obstype_current_numeric_results | 0.426937602 |
| latest_hgb_obstype_current_numeric_results | -0.002141086 |
| latest_combined_bnp_current_numeric_results | 0.137882059 |
| count_emergency_visit_enc_past_encounters_730_days | 0.129271839 |
| latest_tobacco_user_clin_valid_current_any_conditions | 0.246162066 |
| latest_wbc_obstype_current_numeric_results | 0.653423264 |
| length_of_stay_in_days | 0.280443833 |
| count_emergency_visit_enc_past_encounters_365_days | 0.100586839 |
| count_emergency_visit_enc_past_encounters_180_days | 0.108034175 |
| max_combined_bnp_past_numeric_results_90_days | 0.099707536 |
| earliest_albumin_obstype_current_numeric_results | -0.020072411 |
| latest_serum_calcium_obstype_current_numeric_results | -0.097463554 |
| max_pain_score_current_numeric_results | 0.015089961 |
| median_chloride_level_obstype_current_numeric_results | -0.012152238 |
| earliest_wbc_obstype_current_numeric_results | -0.313113794 |
| latest_insulin_med_valid_past_medications | 0.096388674 |
| unknown_instype_insurance_coverage | -0.103816923 |
| count_left_ama_dcdis_past_encounters_730_days | 0.179421717 |
| latest_dementia_clin_valid_current_any_conditions | 0.147858113 |
| min_bmi_historic_numeric_results_180_days | -0.009724662 |
| age_in_years | 0.002548348 |
| trend_troponin_obstype_current_numeric_results | 0.003806751 |
| latest_ccs_cci_3_endocrine_nutritional_metabolic_immunity_clin_valid_current_any_conditions | -0.081652215 |
| latest_ccs_cci_7_circulatory_clin_valid_historic_any_conditions | 0.077387727 |
| median_serum_calcium_obstype_past_numeric_results_730_days | 0.072233567 |
| gender_demographics_male | 0.070186333 |
| max_glucose_obstype_past_numeric_results_90_days | 0.191985278 |
| min_sodium_level_obstype_past_numeric_results_365_days | -0.009255571 |
| count_observation_visit_enc_past_encounters_180_days | 0.068232372 |
| min_pulse_oximetry_obstype_past_numeric_results_90_days | -0.008220321 |
| median_wbc_obstype_historic_numeric_results_365_days | -0.276740572 |
| max_serum_magnesium_obstype_past_numeric_results_90_days | 0.109903744 |
| latest_betaadrenergic_blocking_agents_group_valid_historic_medications | 0.094163902 |
| bin_max_inr_obstype_past_numeric_results_180_days | 0.093564013 |
| latest_trauma_clin_valid_current_any_conditions | -0.125282138 |
| latest_spironolactone_oral_med_valid_historic_medications | 0.076407071 |
| max_platelet_count_obstype_historic_numeric_results_90_days | 0.409223077 |
| latest_ccs_cci_6_nervous_and_sense_clin_valid_current_any_conditions | -0.059777043 |
| latest_potassium_level_obstype_current_numeric_results | 0.053608051 |
| commercial_instype_insurance_coverage | -0.053262611 |
| count_inpatient_visit_enc_past_encounters_365_days | 0.037148385 |
| admission_source_current_encounters_transfer_from_hospital_admsrc | -0.091128352 |
| latest_sodium_level_obstype_current_numeric_results | -0.006422035 |
| latest_transplant_proc_past_procedures | -0.528777955 |
| latest_ccs_cci_7_circulatory_clin_valid_current_any_conditions | -0.052913949 |
| latest_liver_disease_moderate_or_severe_clin_valid_current_any_conditions | 0.189909193 |
| latest_liver_disease_moderate_or_severe_clin_valid_past_any_conditions | 0.195530686 |
| latest_morphine_valid_current_medications | 0.032412742 |
| latest_carbon_dioxide_obstype_current_numeric_results | -0.003958218 |
| latest_stroke_clin_valid_historic_any_conditions | 0.054507852 |
| latest_digoxin_med_valid_administrator_dispenser_current_medications | 0.064175728 |
| latest_loop_diuretics_group_valid_administrator_dispenser_current_medications | 0.029824673 |
| latest_cardiac_cath_and_angiography_proc_past_procedures | 0.035786791 |
| latest_ccs_cci_2_neoplasms_clin_valid_past_any_conditions | -0.068775981 |
| latest_platelet_count_obstype_current_numeric_results | -0.079665994 |
| latest_central_venous_access_proc_past_procedures | 0.032979628 |
| count_observation_visit_enc_past_encounters_365_days | 0.016260435 |
| latest_valvular_heart_disease_clin_valid_current_any_conditions | 0.028786659 |
| latest_antibiotic_misc_pharmacotherapy_med_valid_past_medications | 0.034523916 |
| min_chloride_level_obstype_past_numeric_results_90_days | -0.00272079 |
| latest_morphine_valid_past_medications | 0.011921626 |
| earliest_troponin_obstype_current_numeric_results | 0.023443148 |
| min_chloride_level_obstype_historic_numeric_results_730_days | -0.001516607 |
| latest_glucose_obstype_current_numeric_results | 0.030096805 |
| latest_peripheral_vascular_disease_clin_valid_current_any_conditions | 0.013893523 |
| latest_myocardial_infarction_clin_valid_current_any_conditions | 0.006908058 |

RECEIVE INDICATION OF PATIENT
BEING AN AMI PATIENT ~ 510

ELECTRONICALLY QUERY EHR FOR
FEATURE VALUES ~ 520

GENERATE, UTILIZING ONE OR MORE
MACHINE LEARNING MODELS, A
PREDICTION OF AMI PATIENT BEING
READMITTED ~ 530

BASED ON PREDICTION,
AUTOMATICALLY INITIATE
INTERVENING ACTION(S) TO REDUCE
LIKELIHOOD OF READMISSION ~ 540

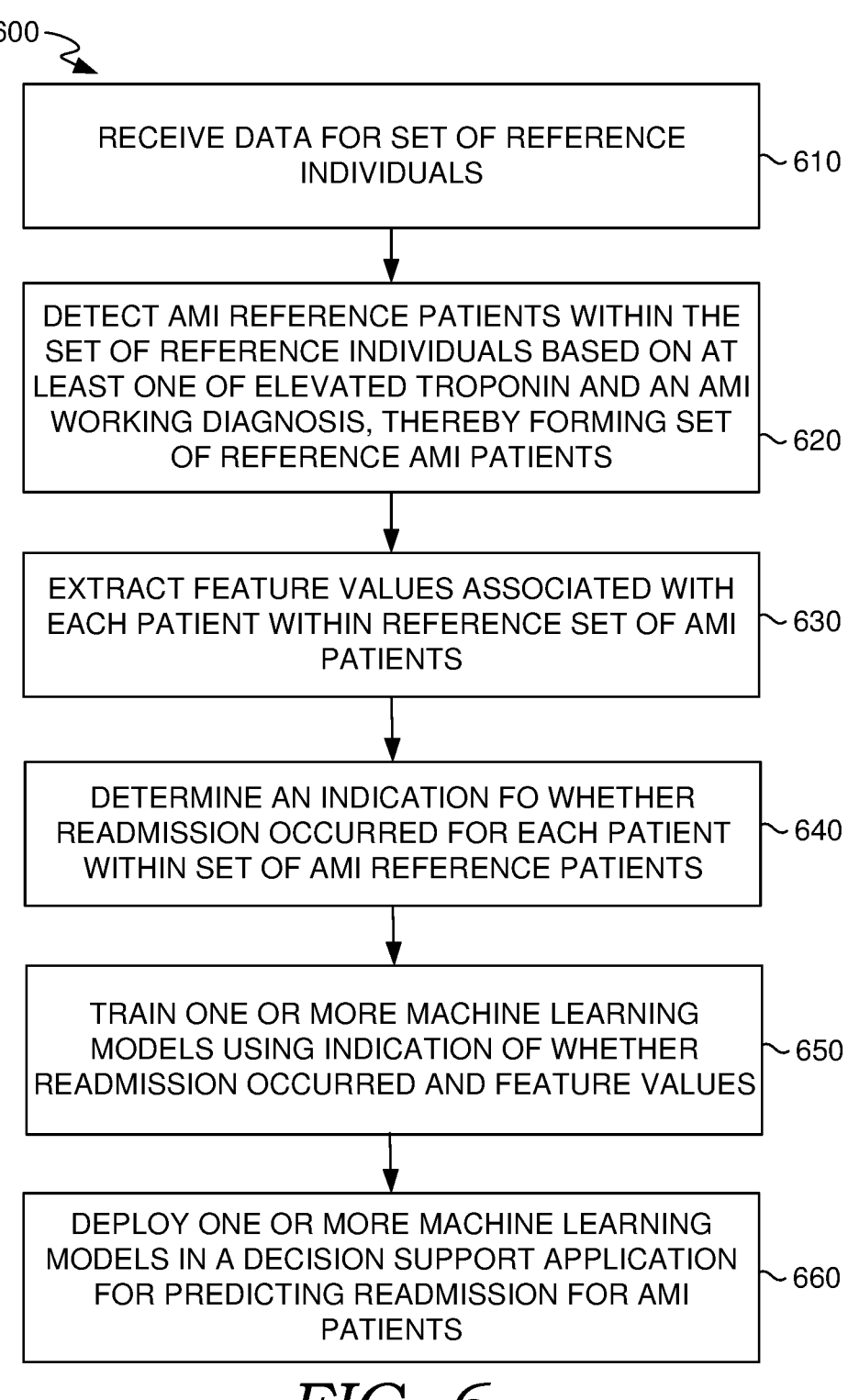

600

RECEIVE DATA FOR SET OF REFERENCE INDIVIDUALS ~ 610

DETECT AMI REFERENCE PATIENTS WITHIN THE SET OF REFERENCE INDIVIDUALS BASED ON AT LEAST ONE OF ELEVATED TROPONIN AND AN AMI WORKING DIAGNOSIS, THEREBY FORMING SET OF REFERENCE AMI PATIENTS ~ 620

EXTRACT FEATURE VALUES ASSOCIATED WITH EACH PATIENT WITHIN REFERENCE SET OF AMI PATIENTS ~ 630

DETERMINE AN INDICATION FO WHETHER READMISSION OCCURRED FOR EACH PATIENT WITHIN SET OF AMI REFERENCE PATIENTS ~ 640

TRAIN ONE OR MORE MACHINE LEARNING MODELS USING INDICATION OF WHETHER READMISSION OCCURRED AND FEATURE VALUES ~ 650

DEPLOY ONE OR MORE MACHINE LEARNING MODELS IN A DECISION SUPPORT APPLICATION FOR PREDICTING READMISSION FOR AMI PATIENTS ~ 660

| SUB MODELS | AUC % | | |
|---|---|---|---|
| | LACE | HOSPITAL SCORE | AMI MODEL |
| ADMIT | -- | 65.12* | 70.0 |
| DISCHARGE | 64.07 | 64.97* | 70.4 |

DECISION SUPPORT TOOLS FOR REDUCING READMISSIONS OF INDIVIDUALS WITH ACUTE MYOCARDIAL INFARCTION

BACKGROUND

Acute myocardial infarction (AMI), which may also be referred to as a heart attack, is caused by diminished flow of blood to the heart and is one of the leading causes of death in the developed world, causing more than one million deaths in the United States annually. Further, a study conducted in 2013 by Healthcare Cost and Utilization Project reported that rate of readmission for AMI patients (which was 14.7%) was 6% higher than the overall readmission rate. Readmissions can reflect that a patient's health is declining, rather than improving, after discharge and may further increase the patient's exposure to risks typically associated with hospital readmissions, such as infection. In addition to negatively impacting the patient's health, AMI readmissions are costly and place administrative and resource burdens on healthcare entities. The 2013 study done by Healthcare Cost and Utilization Project reported that aggregate hospital costs of readmissions following AMI stays was 7 billion. Centers for Medicare & Medicaid Services (CMS) has launched a Hospital Readmissions Reduction Program (HRRP) to reduce avoidable readmissions, lower healthcare costs, and improve patient safety and outcomes by penalizing facilities with higher readmission rates. To reduce readmissions, individuals at risk for readmission may be identified so that interventions may be implemented. However, conventional technologies developed to predict readmission for AMI patients perform poorly, and in particular, have been shown to have poor generalization in real clinical settings and do not effectively enable the necessary interventions because predictions cannot be made until after discharge.

SUMMARY

Systems, methods and computer-readable media are disclosed for providing a decision support tool for reducing readmissions of AMI patients through early prediction of readmission. An AMI patient may be identified using a working diagnosis and/or an elevated troponin level. Utilizing these data features to identify a patient as being an AMI patient enables for AMI patients to be identified earlier during their encounter and readmission to be predicted earlier, thereby increasing the effectiveness of intervening actions. After a patient is identified as an AMI patient, the patient's electronic health record (EHR) may be queried so that data feature values can be extracted and input into one or more machine learning models trained to predict readmission for AMI patients. The models may be trained on data available prior to discharge such that prediction may be reliably determined and provided prior to discharge. More specifically, predictions may be made as early as one day after admission and, in some aspects, sooner, such as 12 hours after admission. Early prediction enables more effective interventions and thus reduces patient mortality. Based on the prediction, an intervening action, such as issuing a notification, generating a recommendation, ordering tests, scheduling a follow-up, and/or modifying discharge or care instructions, may be automatically initiated to reduce the likelihood of readmission.

Further embodiments of the disclosure are directed to training one or more machine learning models to predict readmission of an AMI patient in a computing application such as a decision support tool. Training the models may include identifying AMI cohorts from reference data of a reference population, which may be done based on an AMI working diagnosis and/or elevated troponin. Using these measures for identifying AMI patients increases the training data pool compared to using a principal diagnosis, which creates a more robust learning system. During training, two machine learning models, which may be logistic regression models according to one embodiment, may be trained on different sets of data. For example, a first (admit) model may be trained using AMI reference patient data as it existed at a predetermined time following the patient's admission, such as 12 hours after admission. A second (discharge) model may be trained using AMI reference patient data as it existed at a later time, such as the time of discharge. Feature selection may be performed separately on these models such that different features may be used from the reference data set for these two models. When the trained models are implemented on new data, readmission risk scores (e.g., probabilities) from each model are combined, such as by determining a weighted average of the risk scores.

BRIEF DESCRIPTION OF THE DRAWINGS

The present invention is described in detail below with reference to the attached drawing figures, wherein:

FIG. 3 depicts a schematic illustration of example time intervals for features that may be utilized in predicting readmission for AMI patients, in accordance with an embodiment of the disclosure;

FIGS. 4A and 4B depict example features that may be utilized in predicting readmission for AMI patients, in accordance with an embodiment of the disclosure;

FIG. 6 depicts a flow chart of an example method for training and deploying a machine learning system to predict readmission for AMI patients, in accordance with an embodiment of the disclosure;

DETAILED DESCRIPTION

Figure 1:
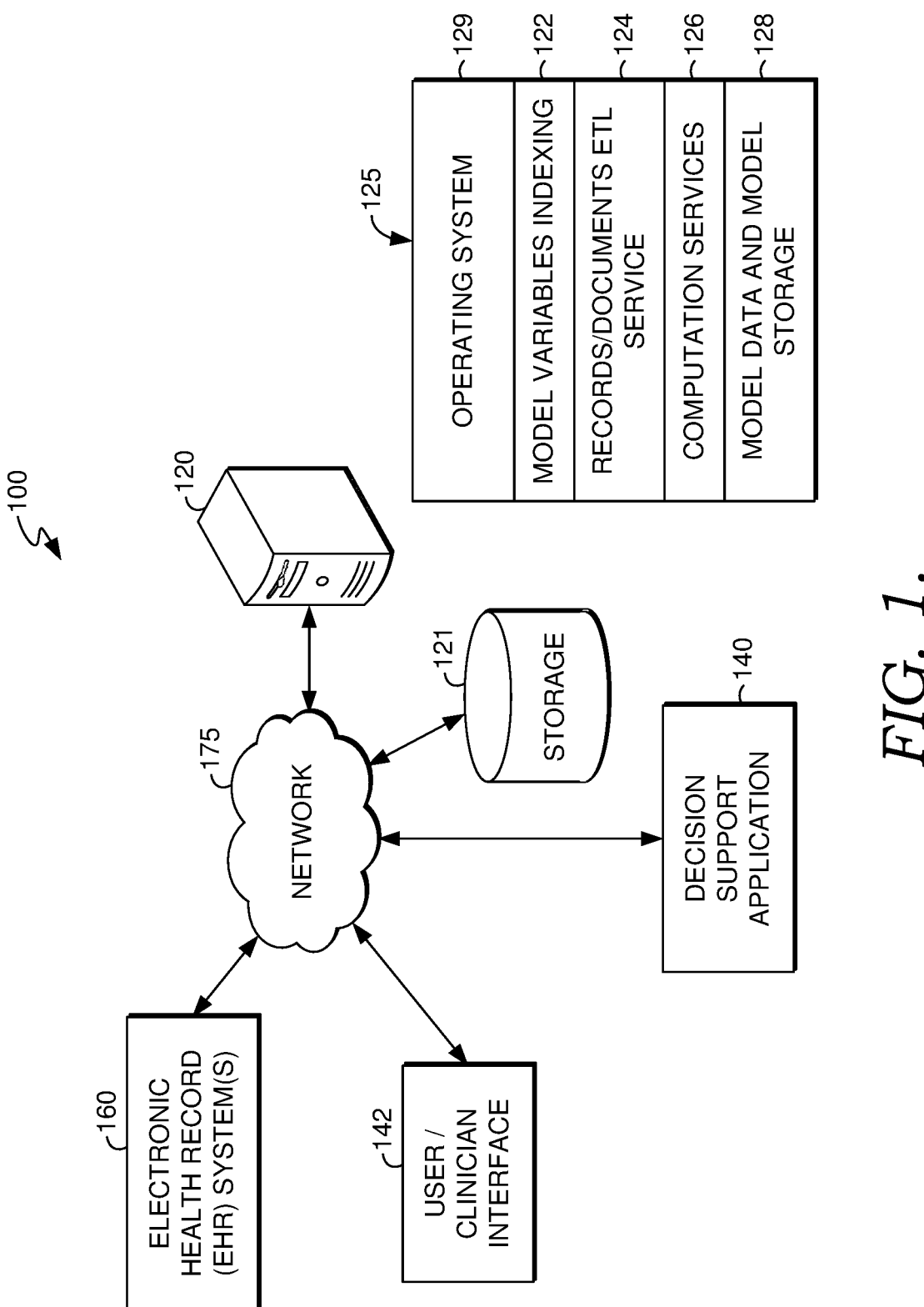
FIG. 1 depicts aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

At a high level, this disclosure describes, among other things, methods and systems for providing decision support for individuals that are having or recently had an AMI. As previously explained, acute myocardial infarction (AMI), which may also be referred to as a heart attack, is caused by diminished flow of blood to the heart due to buildup of various substances (e.g., plaque, fatty substances) in a coronary artery. AMI is one of the leading causes of death in the developed world. Further, a study conducted in 2013 by Healthcare Cost and Utilization Project reported that rate of readmission for AMI patients (which was 14.7%) was 6% higher than the overall readmission rate. Readmissions can indicate that a patient's health is declining, rather than improving, after discharge and may further increase the patient's exposure to risks typically associated with hospital readmissions, such as infection. In addition to negatively impacting the patient's health, AMI readmissions are costly. The 2013 study done by Healthcare Cost and Utilization Project reported that aggregate hospital costs of readmissions following AMI stays was 7 billion. CMS has launched a Hospital Readmissions Reduction Program (HRRP) to reduce avoidable readmissions, lower healthcare costs, and improve patient safety and outcomes by penalizing facilities with higher readmission rates. To reduce improve patient health as well reduce health care costs, individuals at risk for readmission may be identified so that interventions may be implemented to prevent readmissions. However, conventional models developed to predict readmission after AMI have been shown to have poor generalization in real clinical settings and cannot predict readmissions until after discharge or several days into the patient's admittance, at which point interventions to prevent readmission are less effective.

Accordingly, embodiments of the present disclosure aim to accurately identify AMI patients predicted to be readmission within a future time interval, such as 30 days. Further, this identification through embodiments of the disclosure may be done early within a patient's encounter to thereby increase the effectiveness of interventions to reduce a readmission likelihood. An AMI patient may be identified using a working diagnosis and/or an elevated troponin level. Utilizing these features to identify a patient as being an AMI patient enables for AMI patients to be identified earlier during their encounter and readmission to be predicted earlier, thereby increasing the effectiveness of intervening actions. After a patient is identified as an AMI patient, the patient's electronic health record (EHR) may be queried so that feature values can be extracted and input into one or more machine learning models trained to predict readmission for AMI patients. The models may be trained on data available prior to discharge such that prediction may be reliably made prior to discharge. More specifically, predictions may be made in a much shorter amount of time, such as one day after admission and, in some aspects, sooner, such as 12 hours after admission. Early prediction enables more effective interventions. Based on the prediction, an intervening action, such as ordering tests, scheduling a follow-up, and/or modifying discharge or care instructions, may be automatically initiated to reduce the likelihood of readmission.

Further embodiments of the disclosure are directed to training one or more machine learning models to predict readmission of an AMI patient. Training the models may include identifying AMI cohorts from reference data, which may be done based on an AMI working diagnosis and/or elevated troponin. Using these measures for identifying AMI patients increases the training data pool compared to using a principal diagnosis, which creates a more robust learning system. During training, two machine learning models, which may be logistic regression models, may be trained on different sets of data. For example, a first (admit) model may be trained using AMI reference patient data as it existed at a predetermined time following the patient's admission, such as 12 hours after admission. A second (discharge) model may be trained using AMI reference patient data as it existed at a later time, such as the time of discharge. Feature selection may be performed separately on these models such that different features may be used from the reference data set for these two models. When the trained models are implemented on new data, readmission risk scores (e.g., probabilities) from each model are combined, such as by determining a weighted average of the risk scores.

Referring now to the drawings generally and, more specifically, referring to FIG. 1, an aspect of an operating environment 100 is provided suitable for practicing an embodiment of this disclosure. Certain items in block-diagram form are shown more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure aspects of the invention. Thus, for readability, items are shown and referenced in the singular (while fully contemplating, where applicable, the plural).

As shown in FIG. 1, example operating environment 100 provides an aspect of a computerized system for compiling and/or running an embodiment of a computer-decision support tool for reducing AMI patient readmissions. Environment 100 includes one or more electronic health record (EHR) systems 160, such as a hospital EHR system, communicatively coupled to a network 175, which is communicatively coupled to a computer system 120. In some embodiments, components of environment 100 that are shown as distinct components may be embodied as part of or within other components of environment 100. For example, EHR systems 160 may comprise one or more EHR systems, such as hospital EHR systems, health information exchange EHR systems, ambulatory clinic EHR systems, cardiac EHR systems. Such EHR systems 160 may be implemented in computer system 120. Similarly, EHR system 160 may perform functions for two or more of the EHR systems (not shown).

Network 175 may comprise the Internet, and/or one or more public networks, private networks, other communications networks such as a cellular network, or similar network for facilitating communication among devices connected through the network. In some embodiments, the configuration of network 175 may be determined based on factors such as the source and destination of the information communicated over network 175, the path between the source and destination, or the nature of the information. For example, intra-organization or internal communication may use a private network or virtual private network (VPN). Moreover, in some embodiments, items shown as being communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health records, which may be stored on storage 121, and may further include one or more computers or servers that facilitate the storing and retrieval of health records. In some embodiments, EHR system 160 may be implemented as a cloud-based platform or may be distributed across multiple physical locations. EHR system 160 may further include record systems that store real-time or near real-time patient (or user) information, such as information recorded from sensors on wearable, bedside, or in-home patient monitors, for example. Although FIG. 1 depicts an exemplary EHR system 160 that may be used for storing patient information, it is contemplated that an embodiment may also rely on a decision support application 140 for storing and retrieving patient record information.

Example operating environment 100 further includes a user/clinician interface 142 communicatively coupled through network 175 to EHR system 160. Although environment 100 depicts an indirect communicative coupling between user/clinician interface 142 and EHR system 160 through network 175, it is contemplated that one embodiment of user/clinician interface 142 is communicatively coupled to EHR system 160 directly. An embodiment of user/clinician interface 142 takes the form of a graphical user interface operated by a software application or set of applications (e.g., decision support application 140) on a computing device. In an embodiment, the application includes the PowerChart® software manufactured by Cerner Corporation. In an embodiment, the application is a Web-based application or applet. User/clinician interface 142 facilitate accessing and receiving information from a user or healthcare provider about a specific AMI patient or set of AMI patients for which the likelihood of being readmitted is predicted according to the embodiments presented herein. Such information may include patient history; healthcare resource data; physiological variables (e.g., vital signs) measurements, time series, and predictions (including plotting or displaying the determined outcome and/or issuing an alert) described herein; or other health-related information, and facilitates the display of results, recommendations, or orders, for example. In an embodiment, user/clinician interface 142 also facilitates receiving orders, such as orders for more resources, from a user based on the results of predictions. User/clinician interface 142 may also be used for providing diagnostic services or evaluation of the performance of various embodiments.

An embodiment of decision support application 140 comprises a software application or set of applications (which may include programs, routines, functions, or computer-performed services) residing on a client computing device, on one or more servers in the cloud, or distributed in the cloud and on a client computing device such as a personal computer, laptop, smartphone, tablet, mobile computing device, front-end terminals in communication with back-end computing systems or other computing device(s) such as computer system 120 described below. In an embodiment, decision support application 140 includes a Web-based application or applet (or set of applications) usable to provide or manage user services provided by an embodiment of the invention. For example, in an embodiment, decision support application 140 facilitates processing, interpreting, accessing, storing, retrieving, and communicating information acquired from EHR system 160 or storage 121, including predictions and condition evaluations determined by embodiments of the invention as described herein. In an embodiment, decision support application 140 sends a recommendation or notification (such as an alarm or other indication) directly to user/clinician interface 142 through network 175. In an embodiment, decision support application 140 sends a maintenance indication to user/clinician interface 142. In some embodiments, decision support application 140 includes or is incorporated into a computerized decision support tool, as described herein. Further, some embodiments of decision support application 140 utilize user/clinician interface 142. For instance, in one embodiment of decision support application 140, an interface component, such as user/clinician interface 142, may be used to facilitate access by a user (including a clinician or patient) to functions or information on a sensor device, such as operational settings or parameters, user identification, user data stored on the sensor device, for example.

In some embodiments, decision support application 140 utilizes user/clinician interface 142 to facilitate accessing and receiving information from a user or clinician about a specific patient, a set of patients, or a population according to the embodiments presented herein. Decision support application 140 and/or user/clinician interface 142 also facilitates the display of results, recommendations, or orders, for example. In an embodiment, decision support application 140 also facilitates receiving orders, scheduling time with clinicians (including follow up visits), or queries from a user, based on the results of a predicted readmission risk, which may utilize user/clinician interface 142 in some embodiments.

Example operating environment 100 further includes computer system 120, which may take the form of a server, which is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations such as one or more local clients and one or more remote servers and may be distributed across the other components of example operating environment 100. For example, a portion of computer system 120 may be embodied on the computer system supporting decision support application 140. In one embodiment, computer system 120 comprises one or more computing devices, such as a server, desktop computer, laptop, or tablet, cloud-computing device or distributed computing architecture, a portable computing device such as a laptop, tablet, ultra-mobile PC, or a mobile phone.

Embodiments of computer system 120 include computer software stack 125, which, in some embodiments, operates in the cloud as a distributed system on a virtualization layer within computer system 120, and includes operating system 129. Operating system 129 may be implemented as a platform in the cloud and is capable of hosting a number of services such as services 122, 124, 126, and 128, described further herein. Some embodiments of operating system 129 comprise a distributed adaptive agent operating system. Embodiments of services 122, 124, 126, and 128 run as a local or distributed stack in the cloud, on one or more personal computers or servers such as computer system 120, and/or a computing device running user/clinician interface 142 and/or decision support application 140. In some embodiments, user/clinician interface 142 and/or decision support application 140 operate in conjunction with software stack 125.

In embodiments, model variables indexing service 122 provide services that facilitate retrieving frequent itemsets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, model variables indexing service 122 may invoke computation services 126. Predictive models service 124 is generally responsible for providing one or more models for predicting readmission of AMI patients as described in connection to decision support tool 200 of FIG. 2 and/or methods 500, 600, and 800 of FIGS. 5, 6, and 8 respectively.

Computation services 126 perform statistical software operations, such as computing the transformed variable predictions, transferred features (such as log and log 1p functions of features), and severity or risk indices as described herein. In an embodiment, computation services 126 and predictive models service 124 include computer software services or computer program routines. Computation services 126 also may include natural language processing services (not shown) such as Discern nCode™ developed by Cerner Corporation, or similar services. In an embodiment, computation services 126 include the services or routines that may be embodied as one or more software agents or computer software routines. Computation services 126 also may include services or routines for using one or more models, including logistic regression models, for predicting AMI patient readmission, such as the models described in connection to FIGS. 2-11.

In some embodiments, stack 125 includes file system or cloud-services 128. Some embodiments of file system/ cloud-services 128 may comprise an Apache Hadoop and Hbase framework or similar frameworks operable for providing a distributed file system and which, in some embodiments, provide access to cloud-based services such as those provided by Cerner Heal the Intent®. Additionally, some embodiments of file system/cloud-services 128 or stack 125 may comprise one or more stream processing services (not shown). For example, such stream processing services may be embodied using IBM InfoSphere stream processing platform, Twitter Storm stream processing, Ptolemy or Kepler stream processing software, or similar complex event processing (CEP) platforms, frameworks, or services, which may include the use of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which, in some embodiments, includes patient data for a candidate or target patient (or information for multiple patients), including raw and processed patient data; variables associated with recommendations; recommendation knowledge base; recommendation rules; recommendation update statistics; an operational data store, which stores events, frequent itemsets (such as "X often happens with Y", for example), and itemsets index information; association rulebases; agent libraries, solvers and solver libraries, and other similar information including data and computer-usable instructions; patient-derived data; and healthcare provider information, for example. It is contemplated that the term "data" used herein includes any information that can be stored in a computer storage device or system, such as user-derived data, computer usable instructions, software applications, or other information. In some embodiments, storage 121 comprises data store(s) associated with EHR system 160. Further, although depicted as a single storage store, storage 121 may comprise one or more data stores, or may be in the cloud.

In some embodiments, computer system 120 is a computing system made up of one or more computing devices. In some embodiments, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
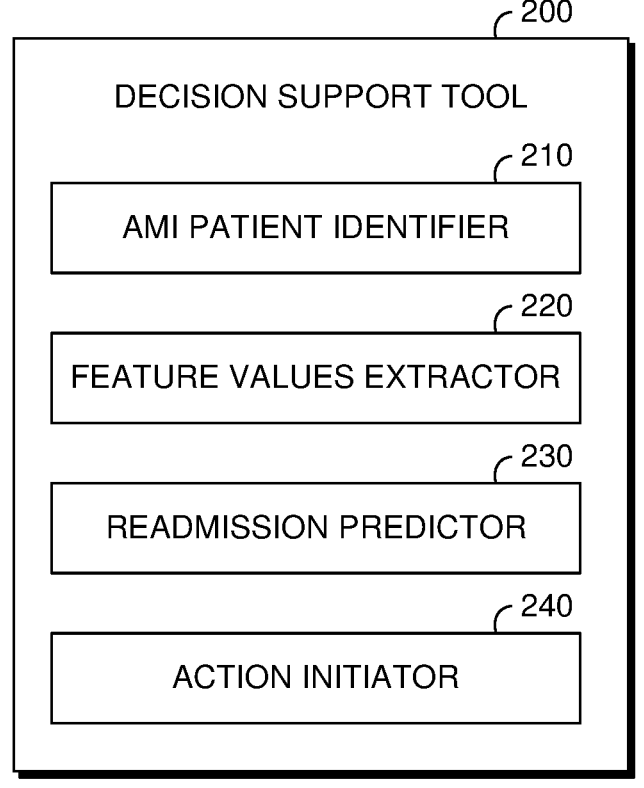
FIG. 2 depicts an example decision support tool, in accordance with an embodiment of the disclosure.

FIG. 2 depicts an example embodiment of a decision support tool 200 for reducing the risk of readmission for AMI patients. Decision support tool 200 may be embodied as decision support application 140 of FIG. 1. In one embodiment, decision support tool 200 may be integrated into a computing system that is part of a health care facility's (e.g., a hospital) computerized system as described with respect to the operating environment 100 of FIG. 1. Decision support tool 200 includes an AMI patient identifier 210, a feature values extractor 220, and a readmission predictor 230. In some aspects, decision support tool 200 further includes an action initiator 240.

AMI patient identifier 210 is generally configured to determine whether an individual is an AMI patient. In this way, AMI patient identifier 210 may ensure readmission predictor 230 is run only on AMI patients and helps prevent computing resources, such as memory, power, and/or bandwidth, from being inefficiently consumed by running readmission predictor 230 on other types of individuals for which readmission predictor 230 was not specifically trained. Identifying AMI patients also helps ensure an inaccurate readmission prediction is generated for a non-AMI patient, which could disrupt the care of the non-AMI patient.

In exemplary aspects, AMI patient identifier 210 determines that a patient is an AMI patient from an indicator in the patient's EHR or otherwise in information about the patient that is received or accessed. The indicator may be a diagnosis, a lab result, a procedure, or an order that indicates the patient is having or has had an AMI within the recent past (e.g., previous 12 hour, 24 hours, or 48 hours). In one embodiment, the indicator is that the patient is having or has had an AMI during the patient's current encounter at a healthcare facility. In exemplary aspects, AMI patient identifier 210 can make this determination at any time prior to the patient's discharge from the current encounter. In exemplary aspects, an indicator that a patient is currently have an AMI or has had an AMI is associated with the current encounter. In this way, in exemplary implementations, the indicator of AMI determined by AMI patient identifier 210 does not include indicators of a past AMI for which the patient was already treated.

In some embodiments, the AMI patient identifier 210 determines that the patient is an AMI patient based on a working diagnosis for the patient. Conventionally, principal diagnoses have been used to identify AMI patients. A principal diagnosis is the cause for a patient's symptoms as determined after some study. Because clinicians typically consider multiple possible causes during a patient's stay and need additional information before confirming a diagnosis, the principal diagnosis is often not available until 2-7 days after patient discharge. As such, predictions for patients identified by a principal diagnosis would not be effective at promoting interventions to reduce the risk of readmission. A working diagnosis, on the other hand, is a diagnosis being considered by a clinician as mostly likely out of other diagnosis but has not yet been confirmed and/or other diagnoses have not been ruled out. A working diagnosis may be available relatively early during a patient's encounter at a healthcare facility. AMI patient identifier 210 may determine the working diagnosis for a patient is an AMI based on diagnosis information in the patient's EHR. For example, AMI patient identifier 210 may determine a working diagnosis from a diagnosis code in the patient's EMR, such as any 121 ICD-10-CM diagnosis codes. In some embodiments, this working diagnosis is determined by AMI patient identifier 210 at any point during a patient's encounter, including within 12 hours after admission or before discharge.

Some embodiments of AMI patient identifier 210 may utilize lab results alternatively or in addition to a working diagnosis to identify a patient as having or having had an AMI. An exemplary lab result may be cardiac troponin, which are proteins that are released when heart muscle is damaged, such as in event of an AMI. As such, troponin is a biomarker for AMI. In one aspect, cardiac troponin I (cTnI) and/or cardiac troponin T (cTnT) are used as an indicator that a patient had an AMI.

Embodiments of AMI patient identifier 210 may determine whether the patient has an elevated troponin level, which may be determined using the upper reference limit (URL). For example, AMI patient identifier 210 may determine whether a patient's troponin level is above the 99 percentile of the URL for the normal range of the assay being used. If so, AMI patient identifier 210 may identify the patient as being an AMI patient. The normal range of an assay used to determine the URL may be a reference range previously determined for a particular assay. Additionally, it is not uncommon for a patient to have multiple troponin tests performed within a given encounter, and some embodiments of AMI patient identifier 210 will determine a patient is an AMI patient if any of the troponin values within the encounter are above a predetermined elevated troponin level.

In exemplary aspects, AMI patient identifier 210 identifies an AMI patient either through an AMI working diagnosis or elevated troponin level. For instance, a patient may be identified as an AMI patient where the patient's record does not include an AMI working diagnosis but does show elevated troponin or where the patient's record includes an AMI working diagnosis but not an elevated troponin level. It should be understood that an AMI patient may have both an AMI working diagnosis and elevated troponin level. In an another embodiment, AMI patient identifier 210 considers working diagnosis but not troponin level. In another embodiment, AMI patient identifier 210 considers troponin level but not working diagnosis.

After an AMI patient is identified, feature values extractor 220 may extract values for various features predetermined to be relevant to an AMI patients' readmission risk. Feature values extractor 220 may extract these values from the patient's EHR. Additionally or alternatively, feature values extractor 220 may receive some or all feature values directly through a user interface, such as user/clinician interface 142, of decision support tool 200. For example, the patient's values for certain features may be solicited from a user, such as a clinician, through a user interface and such values may be provided to feature values extractor 220 through the interface.

The determination of relevance (or impact or importance) of the features to readmission risk is discussed further below with respect to FIGS. 4A-B, 6, and 800. In example embodiments, feature values extractor 220 determines values for features relating to demographics (e.g., age, gender, race, marital status), benefit coverage, diagnoses, procedures (e.g., coronary artery bypass graft, hip and knee replacement etc.), medications (e.g., fentanyl, morphine, propofol, warfarin, etc.), mediation history, labs (troponin, creatine, BMI), and conditions (diabetes, ischemic heart disease, myocardial infarction, etc.), for example. In one embodiment, feature values extractor 220 specifically extracts values for the following features: BNP, BUN having positive impact, albumin, hemoglobin, sodium and chloride groups, age of patient, count of emergency visits, and length of stay. In some instances, the feature value is directly in the patient's EHR. For example, a pulse oximetry feature value may be the pulse oximetry value that is recorded for the patient in the EHR. In other instances, feature values extractor 220 derives the feature value from information in the patient's EHR. For example, feature values extractor 220 may assign a value, such as a binary value, for a particular category based on the patient's data (e.g., assign a feature value of "1" if the patient is married or does not live alone and a value of "0" otherwise). Feature values extractor 220 may also perform a calculation using the patient's data to derive a feature value. For example, where BMI is not a value in the patient's EHR, BMI may be calculated by feature values extractor 220 using the weight and height values from the EHR.

Some feature values may be for one or more time frames. For example, feature values may be "current", "past" or "historic". FIG. 3 depicts a schematic representation 300 of different windows of time that may be considered when determining feature values in accordance with an example embodiment of feature values extractor 220. A "current" feature value may be a value based on information received during the duration between the index encounter's service date (s.d) and the reference date (r.d). As used herein, an index encounter service date is the date on which the patient's current encounter began (e.g., date of admission, which may be referred to as "begin date" or a date later than admission). As used herein, a "reference date" is the date on which the feature values are extracted (which may be the date the readmission predictor 230 is run). "Current2d" refers to the duration between 2 days before the service date and the reference date. "Past" refers to the duration between the service date and a pre-determined lookback period from the service date. In the example in FIG. 3, the lookback period is 180 days (i.e., 180 days prior to the service date). Longer or shorter lookback periods, such as 365 days or 90 days for example, may be utilized in accordance with other embodiments. "Past2d" refers to the duration between 2 days before the service date and the pre-determined lookback period from the service date. "Historic" may refer to the duration between the index encounter's reference date and the pre-determined lookback period from the reference date. It should be understood that the term "date" used herein may also encompass a datetime.

In an example embodiment, the following feature values are extracted by feature values extractor 220:

Demographic, hospitalization, benefit coverages and general encounter features

Age

Gender: Binarized, where '1' represented if patient is 'male'

Race:

Races considered by include black African American, Caucasian, Hispanic, and other races.

Races may be binarized where '1' represented the presence of that race and '0' represented the absence of a particular race with respect to the current encounter.

Marital Status:

Patient who does not live alone and is either married or has a life partner.

These may be binarized where '1' represented the presence of a marital status and '0' represented the absence Person benefit coverages:

Benefit or insurance coverages that were considered included: Medicare, Medicaid, Commercial, Self-Pay and Other insurances These may be binarized where '1' represented the presence of a coverage and '0' represented the absence with respect to the index admission.

Length of stay and Length of stay of an index encounter being greater than 13 days Counter features for numbers of past encounters in time intervals of 6 months, 1 year and 2 years for encounters of inpatient, emergency department (ED), against medical advice (AMA), and any types.

Number of days since last ED encounter and since last Inpatient encounter.

Diagnoses

Diagnosis associated with index admissions may be fetched from a 'conditions' table.

Below is a list of diagnoses considered as features: myocardial infarction, alcohol drug abuse and dependence, anemia, aneurysm and dissection, anxiety disorder, asthma, av fistula, cardiac arrhythmia, c diff infection, cellulitis, angina, chronic pain, coagulation disorder, coma, COPD and emphysema, cystic fibrosis, dementia, DVT and PE, end stage renal disease, EBSL resistance, esophagitis and GERD, fall history, gi hemorrhage, heart failure, HIV and AIDS, hyperlipidemia, pyelonephritis, leukemia, liver and biliary tract disorder, lupus and polymyalgia rheumatica, malnutrition, MDRO infection, mood disorder, MRSA infection, multiple sclerosis, obesity, osteomyelitis, neurological disorder other, pancreatitis, Parkinson's disease, peripheral vascular disease, personality disorder, pneumonia, pneumonia, pressure ulcer, schizophrenia, psychosis, chronic kidney disease no dialysis, rheumatic disease, sepsis septic shock and sirs, shortness of breath, sickle cell anemia, spinal cord injury, stroke, surgical complication, trauma, VRE infection, WBC disorder, chronic renal failure, depression, diabetes mellitus, glaucoma, hypertension, ischemic heart disease, peptic ulcer, tobacco user, valvular heart disease, cancer, diabetic retinopathy, liver disease mild, liver disease moderate or severe, metastatic disease, retinopathy, palliative care, transplant.

All the above diagnoses may be considered over the time windows of historic, past and current with lookback days of 'none', 30, 90, 180, 365, 730 days.

These may be binarized where '1' represented the presence of a diagnosis and '0' represented the absence with respect to the index admission.

Procedures

Procedures associated with index admissions may be fetched from a 'Procedures' table.

Below is the list of procedures considered as features: central venous access, hip and knee joint replacement, artificial mechanical ventilation, CABG, cardiac cath and angiography, CPR cardioversion oncology treatment, craniotomy, gastrointestinal surgery, palliative care, spine surgery, thoracic aneurysm repair, TPN, tracheostomy, transplant, vascular surgery extremity, ventricular assist device, wound care.

The above procedures may considered over the time windows of historic, past and current with lookback days of 'none', 30, 90, 180, 365, 730 days.

These may be binarized where '1' represented the presence of a procedure and '0' represented the absence with respect to. the index admission.

Medications and Medication History

Medications associated with index admissions may be fetched from a 'Medications' table.

Based on Multum "drug classification", medication hierarchy groups, medication hierarchy and generic medications may be considered.

Medication order record may be determined to be valid. Some implementations may utilize 'valid medication' logic to make this determination. For example, according to one implementation, the valid medication logic may comprises the following:

```
(Medication.stopDate IS NOT NULL
    AND (Medication.status in (ACTIVE_QUAL,ACKNOWLEDGED_QUAL,
    IN_PROGRESS_QUAL,STILL_TAKING_AS_PRESCRIBED_QUAL, SENT_QUAL)
        OR (Medication.status in (COMPLETE_QUAL, SUSPENDED_QUAL,
        INACTIVE_QUAL,DISCONTINUED_QUAL, RESOLVED_QUAL)
            AND Medication.startDate IS NOT NULL)
        OR Medication.status IS NULL)
) OR (
Medication.stopDate IS NULL
```

-continued

```
AND (Medication.status in (ACTIVE_QUAL,ACKNOWLEDGED_QUAL,
IN_PROGRESS_QUAL,STILL_TAKING_AS_PRESCRIBED_QUAL, SENT_QUAL)
    OR Medication.status IS NULL)
)
```

Medication may be determined to be intended to be administered in hospital. Some implementations may utilize 'hospital medication' logic to make this determination. For example, according to one implementation, the hospital medication logic may comprise the following:

```
(Medication.intendedDispenser in ('HOSPITAL_PHARMACY',
'INPATIENT_FLOOR_STOCK'))
AND (Medication.intendedAdministrator = 'PROVIDER')
```

Medication hierarchy groups considered as features may include:
  5ht3 receptor antagonists group, anticoagulants group, beta-adrenergic blocking agents group, cardiovascular agents group, coagulation modifiers group, diuretics group, gastrointestinal agents group, glucose elevating agents group, heparins group, laxatives group, local injectable anesthetics group, loop diuretics group, minerals and electrolytes group, miscellaneous respiratory agents group, miscellaneous uncategorized agents group, neuromuscular blocking agents group, phosphate binders group, plasma expanders group, proton pump inhibitors group, respiratory agents group.
Medication hierarchy considered as features may include:
  albumin human, pantoprazole, sodium chloride, propofol, fentanyl, morphine, midazolam.
Generic medications considered as features may include:
  acetaminophen hydrocodone, antibiotic misc. pharmacotherapy, antiplatelet, digoxin, heparin, hydromorphone, inhaled corticosteroid, insulin, spironolactone oral, warfarin.
The above medications may be considered over the time windows of historic, past and current with lookback days of 'none', 30, 90, 180, 365, 730 days.
These may be binarized where '1' represented the presence of a medication and '0' represented the absence with respect to the index admission.
Codified Observations
  Codified values may be Boolean values that are assigned based on observations made on a patient. These values may be fetched from a results table.
  The codified features considered may include:
    'ability to eat', 'ambulation ability', 'bathing ability', 'dressing ability', physical activity assessment', 'toileting ability', transfer ability'.
  The above codified values may be considered over the time window of historic, past and current with lookback days of 90, 180, 270, 365, 730 days.
Disease Burden Scores
  Charlson comorbidity condition score
  Count of chronic conditions
Lab values
  The lab values may be fetched from the 'Results' table.
    The lab tests values can be accessed using the field 'normalizedValue.typedValue.numericValue.value' in the results table.

The lab tests considered may include:
  albumin, ast, bnp, bun, carbon dioxide, chloride level, glucose, height, hgb, inr, pulse oximetry, pain score, platelet count, potassium level, pro beta natriuretic peptide, serum calcium, serum creatinine, serum magnesium, sodium level, troponin, wbc, weight, ph arterial, ast, hemoglobin a1c, ldh, pco2, ptt.
  The lab tests may be accessed using the field 'resultCode' in the results table.
The lab test features may be fetched for different time windows (historic, past2d and current2d) with different lookback period of 90, 180, 365, 730 days and may be transformed with different aggregate functions as given below:
  Earliest: refers to the initial lab test value taken with respect to the relevant time window, e.g. the initial troponin value recorded in the current time interval.
  Recent: refers to the most recent lab test value taken with respect to the relevant time window, e.g. the recent troponin value recorded in the current time interval.
  Maximum: refers to the maximum of all the lab test values taken with respect to the relevant time window, e.g. the maximum troponin value recorded in the current time interval.
  Minimum: refers to the minimum of all the lab test values taken with respect to the relevant time window, e.g. the minimum troponin value recorded in the current time interval.
  Median: refers to the median of all the lab test values taken with respect to the relevant time window, e.g. the median troponin value recorded in the current time interval.
Vitals may be calculated for different time intervals with different lookback periods along with different aggregate functions, e.g. maximum BMI value in past interval of 365 days.
  BMI: may be calculated using the below formula:

$$BMI = \frac{weight\ (kg)}{[height\ (m)]^2}$$

Pain Score: a value given between '1' to '10' when the resultCode is present in concept 'PAIN_SCORE_OBSTYPE'.
  Pulse Oximetry: an estimate of the amount of oxygen in the blood.
Embodiments of feature values extractor 220 may also perform feature engineering to determine the feature values for the readmission predictor 230. In some embodiments, feature values extractor 220 combines all the different chronic historic conditions time progressions into one feature to get an indication whether patient had any historic chronic disease. In some embodiments, feature values extractor 220 adds explanatory names to chronic conditions features. In some embodiments, feature values extractor 220 creates combined inpatient and observation counts, which may be for 180, 365 and 730 day. In some embodiments, feature values extractor 220 calculates eGFR using following formula:

$$GFR\left(\frac{\frac{mL}{min}}{1.73\ m^2}\right) = 175 \times (S_{cr})^{-1.154} \times$$

$$(age)^{-0.203} \times (0.752 \text{ if female}) \times (1.212 \text{ if African American})$$

In some embodiments, feature values extractor 220 combines certain surgical past medication indicators, such as neuromuscular blocking agents and hydromorphone for different lookback periods (e.g., 30, 90, 180, 365, 730 days). In some embodiments, feature values extractor 220 combines emergency indicators based on the admission type and the encounter type. In some embodiments, feature values extractor 220 creates a "chronic_kidney_disease" indicator feature.

Some embodiments of feature values extractor 220 imputes, clips, and/or transforms features. One embodiment performs gross outlier clips, imputation, and transformation for the certain features as indicated in the tables below.

| Numeric Feature | Normal Clinical Range | Range Clip | Gross Outlier Clips | Imputation | Transformation |
|---|---|---|---|---|---|
| Glucose [mg/dL] | [80-100] fasting [170-200] after eating | Min[40, 100]; Max [80, 800]; Latest, earliest, median [40, 800] | [10, 1500] | Min: 98, Max: 102 else 'median' | Log10p |
| Hemoglobin | [14-18] g/dL male [12-16] g/dL female | Min[5, 15]; Max [10, 15]; Latest, earliest, median [5, 15] | [2, 25] | 12 | (np.where(x.gender_demographics_male == 0, 15./13.7, 1) * x.{x})**2 |
| INR (international normalized ratio) | [~1.1] normal [2-3] with warfarin blood thinner Higher means slower clotting | -- INR threshold 1.2 | [0.7, 15] | 0 | — |
| Pulse Oximetry | [80-100] mmHg | [85, 100] | [1, 100] | 97 | — |
| Platelet Count | [150-400] *10**9 per liter | Min[60, 250]; Max [250, 800]; Latest, earliest, median [60, 800] | [3, 3000] | 250 | Log10p |
| Potassium Level | [3.6, 5.2] millimoles per liter | Min[2.2, 4.2]; Max [3.5, 6.5]; Latest, earliest, median [2.2, 6.5] | [2, 15] | Min: 3.7, Max: 4.5 else 'median' | — |
| Sodium Level (NaCl in medication) | [135, 145] mEq/L | Min[125, 140]; Max [138, 152]; Latest, earliest, median [125, 152] | [100, 165] | If latest_heart_failure and loop_diuretics used: 135 else 138 | — |
| Chloride Level | [96, 106] mEq/L | Min[85, 102]; Max [102, 115]; Latest, earliest, median [85, 115] | [50, 150] | Min: 98, Max: 102 else 'median' | — |
| Serum Calcium | [8.5, 10.5] mg/dL | Min[6.8, 9.5]; Max [8.6, 12]; Latest, earliest, median [6.8, 12] | [4, 16] | 8.6 | — |
| Serum magnesium | [1.7, 2.2] mg/dL | Min[1.3, 2.2]; Max [1.6, 3.4]; Latest, earliest, median [1.3, 3.4] | [0.01, 7] | Min: 2.3, Max: 1.5 else 'median' | — |
| Troponin | [0, 0.4] ng/mL | [0, 100] Trend_troponin feature was added as (Max-Min) troponin | [0, 1000000] | -If latest_heart_failure and loop_diuretics used: 0.3 else 0.001-0 for trend_troponin | Log10p |
| WBC Count | [4,000, 11,000] per microliter of blood Or [4-11] * 10**9 per liter | Min[2.2, 15]; Max [5.3, 40]; Latest, earliest, median [2.2, 40] | [0.5, 150] | Min: 15, Max: 5.3 else 'median' | Log10p |

-continued

| Numeric Feature | Normal Clinical Range | Range Clip | Gross Outlier Clips | Imputation | Transformation |
|---|---|---|---|---|---|
| Albumin | [3.5, 5.5] g/dL Lower implies Kidney or Liver disease | [1.5, 4.5] | [.01, 8] | Min: 4.2 else 'median' | Square |
| ALT | [7, 56] units/L Elevated implies liver damage | [11, 160] *Max current, historic and past included in feature | [3.0, 10000] | 11 | Log10p |
| AST | [10, 40] units/L Elevated implies liver damage, | [11, 160] *Max current, historic and past included in feature | [4.0, 25000] | 11 | Log10p |
| BMI | [18.5, 24.9] Kg/m square >30 is obese | [15, 30] | [10, 90] | 30 | — |
| BNP | [0-100] ng/L | [10, 10000] | [0, 15000] | If latest_heart_failure and loop_diuretics used: 60 else 10 | Log10p |
| BUN | [7-20] mmol/L or mg/dL | Min[15, 50]; Max [7, 160]; Latest, earliest, median [7, 160] | [1, 180] | Min: 15, Max: 7 else 'median' | — |
| Carbon Dioxide | [23-29] mEq/L | Min[14, 25]; Max [25, 40]; Latest, earliest, median [14, 40] | [1, 55] | 25 | — |
| EGFR | [85-110]; Acute renal failure less than 60 mL/min/1.73 m2 | Min[1, 120]; Max [20, 60]; Latest, earliest, median [15, 60] | [1, 300] | Max: 60 else 120 | Log10p |
| Pain Score | [0, 10] [0, 5] no pain [5, 10] worst pain | [0, 10] | — | median | — |
| Charlson comorbidity conditions | each condition assigned a weight from 1 to 6 and summed | [0, 16] | — | — | np.sqrt(x.{x}) |
| ccs_cci_clin | — | [0, 12] | — | — | np.sqrt(4 + x.[x]) |
| age_in_years | — | [18, 95] | — | — | — |
| length_of_stay | — | [1, 14] | — | — | Log10p |
| Days_since features | — | [7, 365*3] | — | 9999 | Log30p |
| Count features | — | [0, floor] (high = floor as fraction not possible) | — | — | Count and past encounters: Log10p |
| Gender | — | — | — | 0 | — |
| medserv | — | — | — | 0 | — |

Using the feature values for a patient from feature values extractor 220, readmission predictor 230 may automatically generate a prediction that the AMI patient will be readmitted within a future time interval. In an example embodiment, the future time interval is 30 days such that the prediction is whether the AMI patient will be readmitted within the next 30 days. In some embodiments, the 30-day period may be 30 days from the time of discharge. In other words, even though the AMI patient may not be discharged when the prediction is made, the prediction may be whether the patient will be readmitted within 30 days of discharge once the patient is discharged in accordance with some embodiments. It is contemplated that other embodiments of readmission predictor 230 may predict readmission in a shorter or longer time interval, either from the date of prediction or date of discharge.

Embodiments of readmission predictor 230 use one or more machine learning models to determine the risk of the AMI patient being readmitted in a future time interval. Readmission predictor 230 may utilize multiple machine learning models that each generate a risk score, and readmission predictor 230 may combine the risk scores from each model to determine an overall risk score for the patient. In exemplary aspects, readmission predictor 230 includes an first model trained on a first subset of patient data and a second model trained on a second subset of patient data. The first and second subsets of patient data may utilize different periods of time. For example, the first model (which may be referred to as an "admit model") may be trained on patient data that existed within a certain time period after the start of the current encounter (i.e., the admission), and the second model (which may be referred to as a "discharge model")

may be trained on patient data that existed at discharge of the patient. In some embodiments, the first model is trained with data known at 12 hours after admission. In other embodiments, a shorter or longer time period may be used after admission, such as 6 hours, 8 hours, 16 hours, or 24 hours. In some embodiments, admission may include either admission for observation or admission to inpatient. Note that these different time frames for data refer to data on which a particular model is trained. In exemplary aspects, during inference, the first (admit) model and the second (discharge) model may be run at the same time for an AMI patient, such as at 12 hours after the start of the encounter (e.g., admission as observation or inpatient). Additionally, both models may be run at any time, not only at a predetermined time (e.g., 12 hours) after admission and/or at discharge.

In exemplary embodiments, the readmission predictor 230 utilizes logistic regression models, such as multivariate logistic regression models. For example, readmission predictor 230 may include a first logistic regression model and a second logistic regression model. In one embodiment, the trained machine learning model(s) are generalized linear models. In one implementation, a GLMnet package is utilized for the final training model. Similar or other types of models may be utilized during training as described further below. In another embodiment, the readmission predictor 230 may utilize a neural network system. It is contemplated that other types of machine learning models may be used in other embodiments.

In some embodiments, different features are used for each model of readmission predictor 230. FIG. 4A depicts a table 400 that lists features that may be utilized by a first (admit) model of an embodiment of readmission predictor 230, and FIG. 4B depicts a table 450 that lists features that may be utilized by a second (discharge) model in this example embodiment. As can be seen, a greater number of feature values may be input into the second model than in the first model. In one example implementation of a trained model for predicting readmission for AMI patients, the first model (e.g., an admit model) utilizes a subset of the set of features in table 400 and has been trained in accordance with the training processes disclosed herein, and the second model (e.g., a discharge model) utilizes a subset of the set of features in table 450 and has been trained in accordance with the training processes disclosed herein. For instance, the first trained model may utilize data indicating whether the patient has a mental condition within a categorized chronic condition category within the current encounter, the number of emergency visits in past encounters within a past time window (e.g., 180 days), the minimum hemoglobin level within a current encounter, whether the patient has a diagnoses or problems of tobacco, patient's age, BNP test results in the current encounter, BNP test results within a past time window (e.g., 365 days), whether the patient has taken and/or been prescribed insulin medication within a historic time window, counter of inpatient encounters, and a max pains score in the current encounter. The second trained model may utilize data indicating data indicating whether the patient has a mental condition within a categorized chronic condition category within the current encounter, the maximum BUN test result within the current encounter, the minimum hemoglobin level within a current encounter, BNP test results in the current encounter, the number of emergency visits in past encounters within a past time window (e.g., 730 days), the number of emergency visits in past encounters within a shorter past time window (e.g., 365 days), the number of emergency visits in past encounters within an evener shorter past time window (e.g., 180 days), whether the patient has a diagnoses or problems of tobacco, the latest white blood count within the current encounter, and the length of stay.

Tables 400 and 450 also include model coefficients in the right-side columns in accordance with one example implementation of a trained model for predicting readmission for AMI. The magnitudes of the coefficients in tables 400 and 450 are reflective of the relative importance of the listed features. Additional details on the training of the models and feature selection is discussed with respect to FIGS. 6 and 8.

Each of the first model and the second model may output a prediction that the AMI patient will be readmitted within the future time interval, and those two predictions may be combined to determine the overall prediction for the AMI patient. In some embodiments, the overall prediction is determined by computing a weighted average of the predictions from the first and second models. In one example, the weights applied to each of the predictions may be time-dependent weights. In other words, the weights may be based on the time since the patient's admission such that the prediction from the first model may be weighed more heavily when the prediction time is closer to admission and weighed less heavily when the prediction time is further from admission.

In one example, the combination of the two predictions are made in accordance with the following computation, where "$LOS_{hrs}$" refers to the time (e.g. in hours that has passed since the start time, $t_{admit}$ refers to the prediction from the first (admit) model, $t_{disch}$ refers to the prediction from the second (discharge) model, IF current encounter type is Observation: $LOS_{switch}=24$;

ELSE: $LOS_{switch}=72$

IF $LOS_{hrs}<LOS_{switch}$:

$$\text{Overall risk score} = \frac{1}{1 + \exp(-(A(LOS_{hrs}) \times t_{admit} + D(LOS_{hrs}) \times t_{disch}))}$$

where:

$$A(LOS_{hrs}) = \left(1 - \frac{LOS_{hrs}}{LOS_{switch}}\right)$$

is the time-dependent contribution weight of the admission score, $$D(LOS_{hrs}) = \left(\frac{LOS_{hrs}}{LOS_{switch}}\right)$$

is the time-dependent contribution weight of the discharge score

IF $LOS_{hrs} \geq LOS_{switch}$:

$$\text{Overall risk score} = \frac{1}{1 + \exp(-t_{disch})}$$

In some embodiments, the "start time" for purposes of determining the $LOS_{hrs}$ in the computation above may be a predetermined time period after admission, such as 12 hours after admission. However, it in other embodiments, the "start time" is the time of admission.

The output of readmission predictor 230 may be in the form of a quantitative risk score, such as a value between 0 and 1. In some aspects, a risk score value between 0 and 1 may be normalized to a value between 0 and 100. This value may reflect a likelihood of the AMI patient being readmitted within predetermined future time interval, such as 30 days. In some embodiments, readmission predictor 230 may output a qualitative risk score in addition to or alternatively to a quantitative score. A qualitative risk score may be determined by comparing a quantitative score to one or more predefined thresholds, where the predefined thresholds correspond to a risk category. For example, in some embodiments, readmission predictor 230 outputs one of the following for a particular AMI patient: no/low risk, medium risk, high risk. In other embodiments, readmission prediction outputs one of the following: no risk, low risk, low-medium risk, medium-high risk, high risk. The predefined thresholds for stratification of the risk categories may be determined based on a predictive positive rate (PPR). In one example, a predefined threshold for a medium risk category is based on a PPR of 40% while a threshold for a high risk category is based on a PPR of 20%. The PPR used here may be based on predictions for a particular facility or care provider institution. In other embodiments, PPR may be based on the reference data during training of the machine learning model(s). In one example, a risk value greater than 0.21 is categorized as high risk, a risk value greater than 0.13 and less than or equal to 0.21 is medium risk, and a risk value less than or equal to 0.13 is low risk.

Based on the readmission risk output by readmission predictor 230, an action may be automatically initiated by action initiator 240. In exemplary aspects, this action is an intervening action intended to modify the course of care to reduce the risk of readmission of the AMI patient. As such, at least one action may occur prior to the patient being discharged. In some embodiments, an intervening action may include emitting or otherwise electronically communicating a recommendation or notification to a caregiver responsible for the patient's care, such as a physician or nurse. This notification may be presented via a user/clinician interface (such as interface 142 described in FIG. 1). The notification may indicate the predicted probability of the AMI patient being readmitted within the future time interval and/or present instructions to not discharge the patient or to discharge patient with particular discharge instructions. Additionally, some embodiments of action initiator 240 may further store the result of the readmission prediction in an EHR associated with the AMI patient and further may include providing the patient's EHR (or facilitating access to the EHR) in the notification.

In example embodiments, an intervening action may include modifying the AMI patient's discharge protocol to one that is designed to reduce the likelihood of readmission. The modified discharge protocol may include requiring additional approval of discharge by a care provider (which may require further examination by a care provider), providing discharge instructions tailored to reduce the risk of readmission relating to the AMI, scheduling a follow up appointment with a care provider within a specified time from discharge, ordering additional testing, and prescribing medications designed to reduce the risk of infection or AMI-related complications from developing. As such, an intervening action may include scheduling a time for a care provider to see the patient prior to discharge or scheduling a follow-up appointment within a designated time period that is less than the time period (e.g., 30 days) for which readmission is predicted. An intervening action may also include electronically adding one or more documents with special discharge instructions to a queue associated with the patient's record, which may include a queue designating documents for printing and/or providing to the patient. One or more care providers, such as a discharge nurse or care coordinator, may be notified of the additional documentation. Further, orders for additional testing to confirm the increased risk of readmission and/or medications may be generated prior to patient's discharge.

One or more of these intervening actions may be performed by automatically modifying computer code executed in a healthcare software program for treating the patient and/or discharging planning, thereby transforming the program at runtime. For example, in one embodiment, the modification comprises modifying (or generating new) computer instructions to be executed at runtime in the program, the modification may correspond to a change in a discharge procedure due to the predicted readmission.

In some embodiments, the intervening actions may be initiated automatically when the probability of readmission satisfies a threshold level (i.e., a threshold risk). The threshold level may vary depending on the action. For instance, a threshold level may be set for providing additional discharge instructions such that, when the threshold is satisfied, an action for providing additional discharge instructions is automatically initiated. A different threshold, such as a higher risk probability, may be set for initiating an exam by a care provider to approve discharge and/or for ordering additional testing. As used herein, satisfying a threshold may refer to meeting or exceeding a threshold value. The thresholds defined for initiating actions may align with the thresholds for qualitative risk scores as previously described above, or they may be independent of those.

Figure 5:
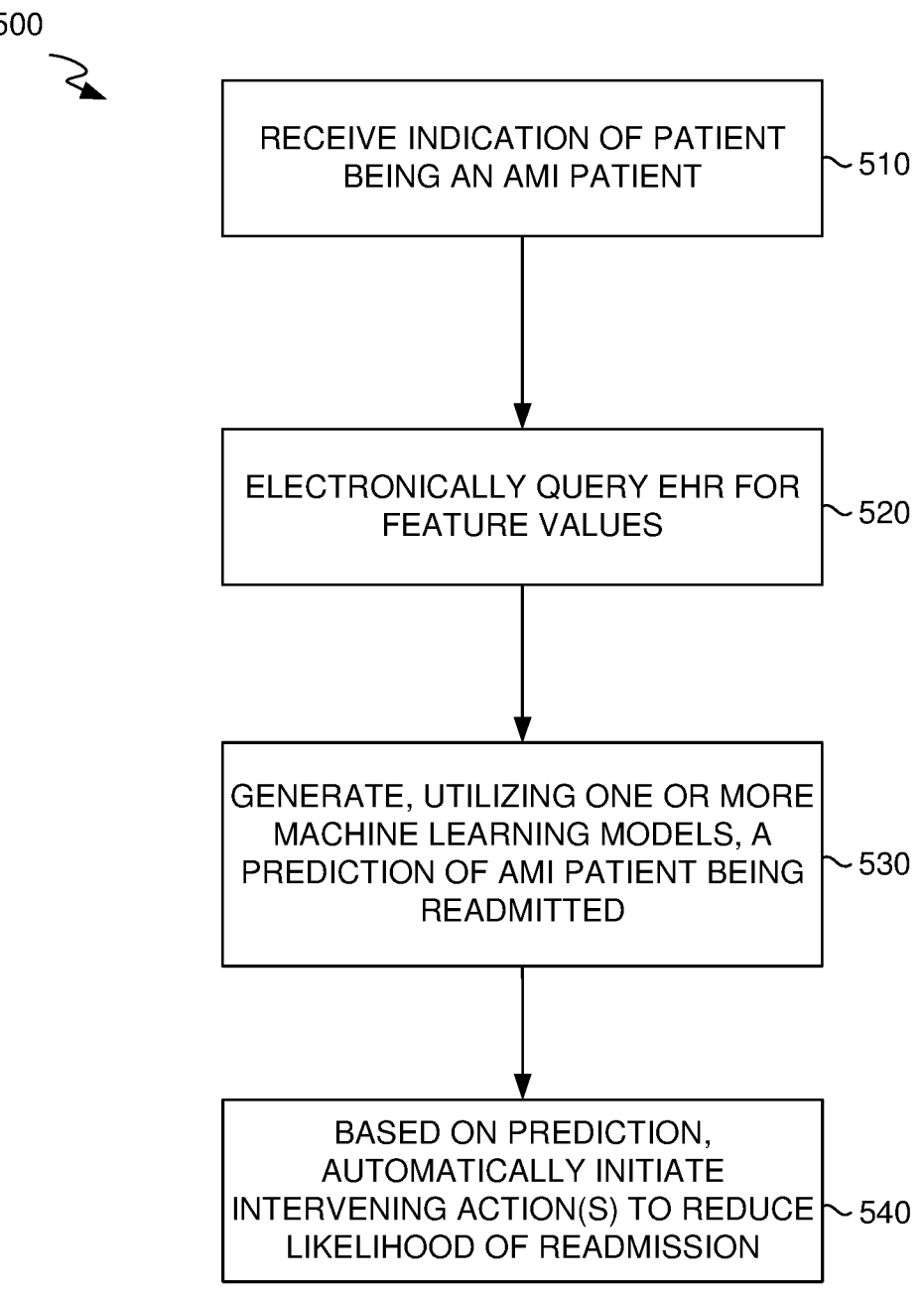
FIG. 5 depicts a flow chart of an example method for predicting whether an AMI patient will have a readmission within a future time interval, in accordance with an embodiment of the disclosure.

Turning now to FIG. 5, a flow diagram is provided to show an example embodiment of a method 500 for early intervention to reduce readmission risk for AMI patients. In example aspects, method 500 may be performed not only for patients who have been admitted to inpatient hospital settings but also for patients admitted for observation, which improves upon technologies that do not reliably work for patients admitted for observation. Embodiments of method 500 is performed, for example, by one or more components of decision support tool 200 in FIG. 2. Method 500 and other methods disclosed herein, such as methods 600 and 800, may be performed by various modules as indicated below. In some embodiments, some or all of these modules correspond to different functions performed by the same hardware components, such as the same processor on a computing device, which may be a user device or a remote server. Additionally or alternatively, some or all of these modules correspond to different hardware components, such as different processors on the same or different computing devices.

Method 500 generally utilizes one or more machine learning models to determine an AMI patients' risk of readmission based on feature values known early within a patient's encounter. Because the risk of readmission may be determined earlier than conventional technology would otherwise allow, method 500 may be suitable for implementation as a computer-performed decision support tool or application for providing care to AMI patients and/or decision planning on AMI patients to more effectively and efficiently reduce the risk of readmission through intervening actions.

In accordance with method 500, at step 510, an indication of that the patient is an AMI patient is received. Step 510 may be performed by an embodiment of AMI patient identifier 210 of FIG. 2 and, as such, embodiments of step 510 may be performed as described with respect to AMI patient identifier 210. The indicator received at step 510 may be a diagnosis, a lab result, a procedure, or an order that indicates the patient is having or has had an AMI. In one embodiment, the indicator is that the patient is having or has had an AMI during the patient's current encounter at a healthcare facility. The indication received at step 510 may be an indication associated with the current encounter such that it indicates the patient is currently have an AMI or has had an AMI within a recent time frame. In this way, in exemplary implementations, the indication of AMI received at step 510 does not include indications of a past AMI for which the patient was already treated.

In some embodiments, the indicator is a working diagnosis for the patient, which may be in the patient's EHR. For example, a working diagnosis may be determined at step 510 from a diagnosis code in the patient's EMR, such as any 121 ICD-10-CM diagnosis codes. Additionally or alternatively, a lab result indicative of AMI may be received at step 510. In example embodiments, step 510 includes determining a patient has an elevated troponin level, which may be determined using the URL for cTnI and/or cTnT. For example, it may be determined whether a patient's troponin level is above the 99 percentile of the URL for the normal range of the assay being used. If so, the patient may be identified as an AMI patient at step 510. In exemplary aspects, an AMI patient can be identified either through an indicator of an AMI working diagnosis or an elevated troponin level.

At step 520, an EHR for the patient is electronically queried for feature values. Step 520 may be automatically performed after an AMI patient is identified by the indicator received at step 510 in accordance with some embodiments. Additionally, step 520 may be performed by some embodiments of feature values extractor 220 of FIG. 2 and, therefore, may be performed in accordance with the details discussed in reference to FIG. 2. These feature values may be extracted from the patient's EHR and/or directly through a user interface. The features for which values are queried at step 520 may relate to demographics, benefit coverage, diagnoses, procedures, medications, mediation history, labs, and conditions, for example. Further, feature values may be queried for one or more predefined time frames, such as current, past, and historic time frames as described with respect to feature values extractor 220. In some aspects, method 500 may further includes imputing clipping, and/or transforming feature values in accordance with one or more predefined algorithms as described herein.

At step 530, method 500 includes automatically generating, utilizing one or more machine learning models, a prediction of the patient being readmitted within a future time interval, where the prediction is based on the feature values for the patient. In some aspects, step 530 is performed at a time less than five days after admission of a patient to a care facility. In exemplary aspects, step 530 may be performed within a day after admission or in an even shorter time period, such as within 12 hours after admission. Step 530 may be performed by embodiments of readmission predictor 230 and as described in reference to FIG. 2.

In some aspects, step 530 includes generating a prediction using a trained logistic regression model. Further, embodiments of step 530 may include determining a first prediction of readmission from a first machine learning model, determining a second prediction of readmission from a second machine learning model trained on a different subset of data as the first machine learning model, and computing an overall readmission risk by combining the first and second predictions. The first machine learning model may be trained using data that was available within a predefined period, such as 12 hours, after admission of the patient, while the second machine learning model may be trained using data that was available at the time of discharge. Additionally, in one example, the first and second predictions are combined using a weighted average, which may be weighted in accordance with time-dependent weights.

At step 540, based on the prediction from step 530, one or more intervening actions are automatically initiated to reduce a likelihood of readmission. Step 540 may be performed by embodiments of action initiator 240 described with respect to FIG. 2. This action initiated at step 540 may be intended to modify the treatment protocol or course of care for the patient in order to reduce the risk of readmission. As such, at least one action may occur prior to the patient being discharged. In some embodiments, an intervening action initiated at step 540 may include emitting or otherwise electronically communicating a recommendation or notification to a caregiver responsible for the patient's care, such as a physician or nurse, which may include a quantitative or qualitative risk score as previously described. This notification may be presented via a user/clinician interface (such as interface 142 described in FIG. 1). Additionally or alternatively, an intervening action may include modifying the AMI patient's discharge protocol to one that is designed to reduce the likelihood of readmission such as by, for example, requiring additional approval of discharge by a care provider (which may require further examination by a care provider), providing discharge instructions tailored to reduce the risk of readmission relating to the AMI, scheduling a follow up appointment with a care provider within a specified time from discharge, ordering additional testing, and/or prescribing medications designed to reduce the risk of infection or AMI-related complications from developing. In some aspects, the intervening action may include electronically adding one or more documents with special discharge instructions to a queue associated with the patient's record and, in some embodiments, notifying a caregiver, such as a discharge nurse and/or care coordinator, of the additional documentation.

FIG. 6 provides a flow diagram depicting an example embodiment of a method 600 for training and deploying one or more machine learning models to predict whether AMI patients will be readmitted. Embodiments of method 600 may be performed, for example, by one or more components of decision support tool 200 in FIG. 2. In some embodiments, a training component, which may be part of computer system 120 within operating environment 100 of FIG. 1, may perform method 600, and the machine learning model(s) trained in accordance with method 600 may be implemented by embodiments of decision support tool 200.

At step 610, data for a set of reference individuals is received. This data may be received from a data base, such as storage 121 of FIG. 1. This data represents potential training data for training one or more machine learning models to predict whether an AMI patient will be readmitted. However, information for patients without AMI may be included within this data set, and it may be appropriate to filter out the data to include only training data for AMI patients. As such, at step 620, AMI patients are detected from the set of reference individuals to form a set of reference AMI patients. Detecting an AMI patient may be based at least one of an elevated troponin level and an AMI working diagnosis. Step 620 may be performed by an embodiment of AMI patient identifier 210 used for training purposes, and as such, the details described in conjunction with AMI patient identifier 210 may apply to the performance of step 620.

Figure 7:
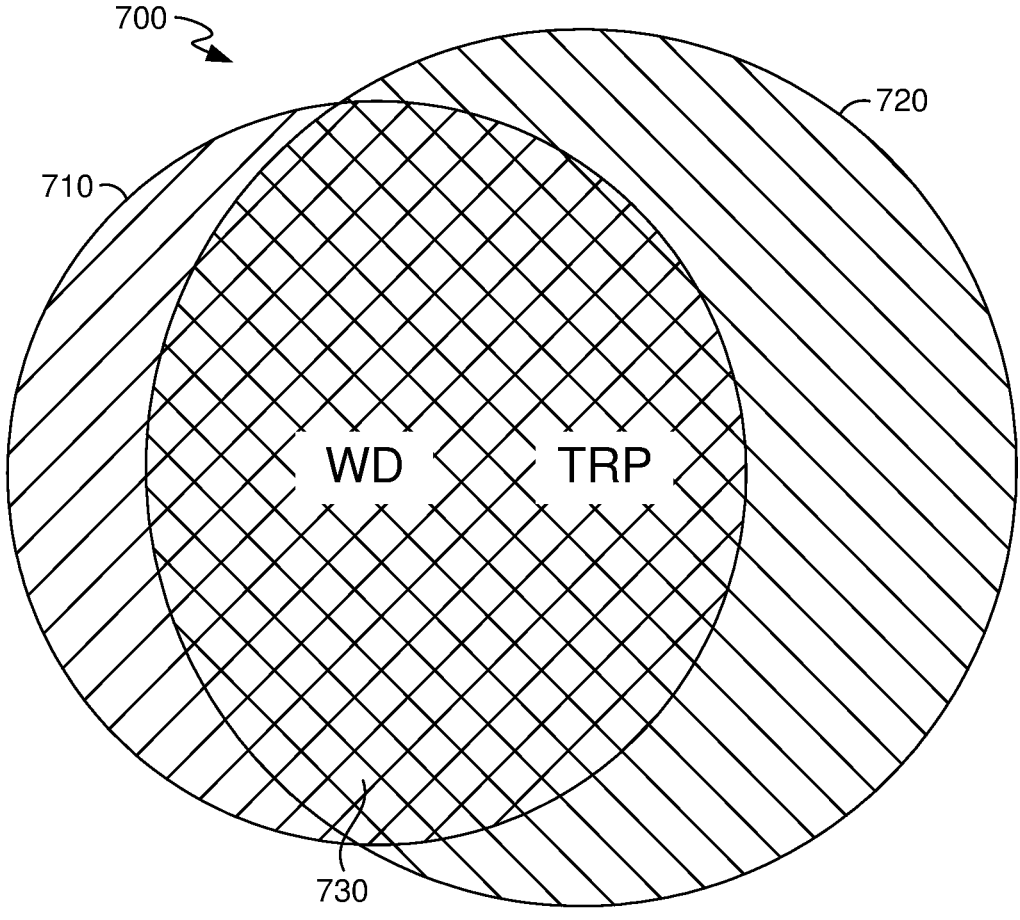
FIG. 7 depicts a schematic illustration of the overlap between a training AMI cohort identified with working diagnosis and an AMI cohort identified with elevated troponin, in accordance with an embodiment of the disclosure.

As previously discussed with respect to AMI patient identifier 210, technology that only identifies AMI patients based on a principal diagnosis for AMI will not identify AMI patients early enough. Further, relying on working diagnosis for AMI only may not capture all potential AMI patients. FIG. 7 provides a graphical illustration 700 showing a population 710 of patients identified using working diagnosis of AMI versus a population 720 of patients identified using elevated troponin as described herein. As illustrated in FIG. 7, there is significant overlap 730 between the two populations, which shows that elevated troponin is a good marker for AMI diagnosis. Additionally, population 720 includes additional patients not identified through work diagnosis only. As such, by using elevated troponin as one referred to herein as a "readmission encounter" and may include the first qualifying inpatient or observation visit within a time period, such as 30 days, of the index admission. In some aspects, an index admission may refer to any qualifying admission to a care facility (which may be limited to an acute care hospital in some embodiments) that is assessed for the outcome of whether a patient was readmitted or not within 30 days. Additionally, in some embodiments, index admissions also include observation stay encounters even if the patient was not officially admitted. By including observation encounters in training, the machine learning model can accurately predict readmissions for AMI patients who were not fully admitted but had an observation stay. The table below provides example criteria that is applied in some aspects of method 600 in identifying an index admission and readmission encounter.

| Visit Type | Inclusion Criteria | Exclusion Criteria |
|---|---|---|
| Index Admission | Age >=18 | Discharge disposition is 'hospice', 'expired', 'transferred to another inpatient facility' and 'left against medical advice' |
| | Encounter type: Inpatient or Observation | Encounter has excluded hospital services (e.g., hospice, psychiatric, sleep, transplant, OB, pediatric, special care baby, neonatology, skilled nursing, clinical oncology, radiotherapy, rehab) |
| | LOS >=12 hours and at least one midnight stay | Encounter has excluded procedures as per CMS |
| | Admission facility is not a rehab, pediatric, behavioral health, psychiatric care, clinics or cancer centers | Encounter has excluded conditions as per CMS |
| Readmission Encounter | Readmission is within 30 days of index admission | Readmission is planned as per CMS Planned Readmission Algorithm |
| | LOS >=12 hours and at least one midnight stay | Readmission occurred within 4 hours of index admission and within the same facility |
| | Readmission facility is not a rehab, pediatric, behavioral health, psychiatric care, clinics or cancer centers | Readmission occurred at a different facility from where index admission occurred |
| | | Readmission has excluded procedures or conditions as per CMS (e.g., transplant services, condition or procedure; OBGYN or Pediatric service or OB condition or procedure; HIV condition; cancer services or condition; rehab service; sleep service; psychiatric service) | method of identifying AMI patients, more patients may be captured for not only identifying training data in step 620 but also for making readmission predictions in the future.

At step 630, feature values for each patient within the reference set of AMI patients may be extracted from the reference data. The feature values may related to an encounter in which the patient has an AMI indicator as described above, and some feature values may related to prior or historical encounters. Step 630 may be performed by an embodiment of feature values extractor 220. As such, the feature values extracted at embodiments of step 630 may include any values for any of the types of features, including associated time periods, described in connection to feature values extractor 220.

At step 640, an indication of whether a readmission occurred for each patient within the set of AMI reference patients may be determined. This readmission may be If an index encounter for a patient has any qualifying readmission encounter, the readmission outcome may be labeled "yes"; otherwise, the outcome may be labeled "no". In some embodiments, the readmission must have a length of stay of at least 12 hours and at least one midnight stay to quality as a readmission encounter. These labels or indications of readmission may effectively service as ground truth for training the machine learning models.

As such, at step 650, one or more machine learning models are trained utilizing, for at least a subset of patients within the set of AMI reference patients, the indications of whether readmission occurred and the extracted feature values. Training the machine learning model(s) includes generating a readmission prediction for an AMI reference patient within the set of AMI reference patients, and then updating one or more coefficients of the machine learning model(s) based on a comparison of the generated prediction and an indication of whether the particular AMI reference patient had a qualifying readmission. The first step of generating the prediction may be performed as described with respect to readmission predictor 230 of FIG. 2. As such, the one or more machine learning models utilized at step 650 may be logistic regression models. Further, in some example embodiments, step 650 includes generating predictions from multiple machine learning models. Each prediction may be generated based on a unique subset of the AMI reference patient's data. For example, a first machine learning model may generate a prediction based on data for the AMI reference patient that was available within a certain time period, such as 6 hours, 8 hours, 12 hours, 16 hours, or 24 hours, after the start of the current encounter (i.e., admission), and a second machine learning model may generate a prediction based on data that was available at the time of the AMI reference patient's discharge. Each of these predictions may be compared to the indicator, in the AMI reference patient's data, of whether or not the AMI reference patient was actually readmitted. The comparison may be represented by a loss value which may then be utilized to update one or more coefficients on the respective model to reduce the loss in future iterations of the machine learning models.

Embodiments of method 600 may further include performing feature selection for the one or more machine learning models. Feature selection may identify a set of features that are the most relevant for reliably predicting readmission for an AMI patient utilizing the machine learning model(s). In embodiments in which there are multiple machine learning models, feature selection may be performed on each model. As such, each model may use feature values for different sets of features. For example, table 400 of FIG. 4A lists features that may be utilized by an embodiment of a first (admit) machine learning model, and table 450 of FIG. 4B lists a different set of features that may be utilized by an embodiment of a second (discharge) model. Further discussion of feature selection is provided with connection to FIG. 7.

Following training of the machine learning model(s), the trained machine learning model(s) may be deployed in a decision support application for predicting readmissions for AMI patients, as shown at step 660. In example aspects, deployment refers to when the one or more trained machine learning models are configured for and released to operate on a computer system supporting the decision support tool, such an embodiment of decision support application 140 on computing system 120 of FIG. 1.

In embodiments in which there are multiple machine learning models, such as an admit model and a discharge model, the models are run at the same time, which may be prior to discharge. That is, even though the models may be trained using feature values that existed at different time periods, the models may operate at the same time during deployment. The models may run as early as one day after admission or, in some implementations, as early as 12 hours after admission in accordance. Each of the machine learning models may output a prediction, which may be referred to as a risk level, and these predictions may be combined to determine an overall prediction of readmission for an AMI patient.

Based on a prediction of readmission generated for an AMI patient during deployment of the one or more machine learning models, one or more intervening actions may be initiated. This step may be performed by an embodiment of action initiator 240 of FIG. 2 and, as such, details described with respect to action initiator 240 may apply to this step. Additionally, initiating an action based on a readmission prediction during deployment under step 660 may be performed similarly as described with respect to step 540 of FIG. 5.

Figure 8:
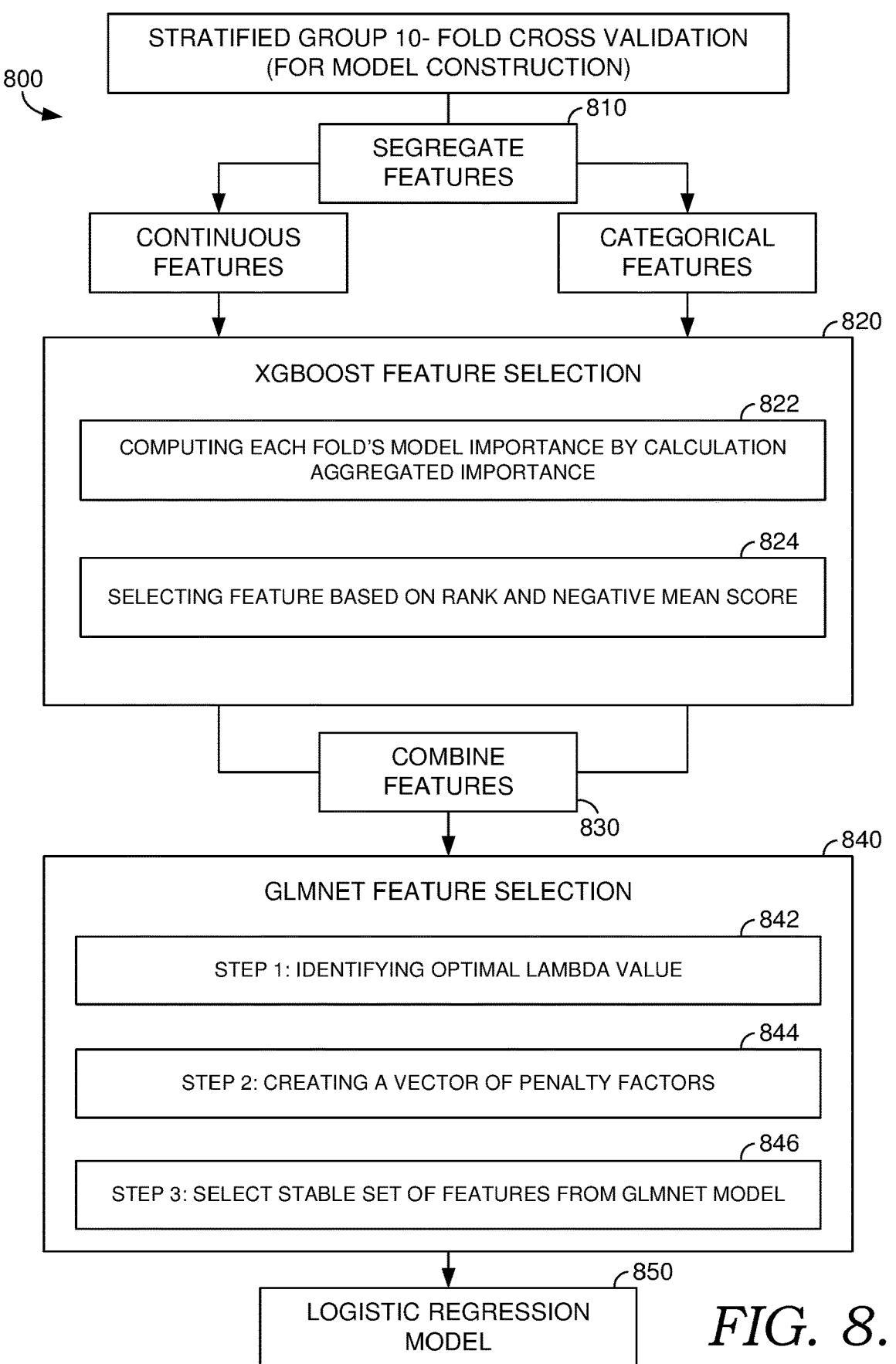
FIG. 8 depicts a diagram of an example method for training a machine learning system to predict readmission for AMI patients, in accordance with an embodiment of the disclosure.

FIG. 8 provides a diagram for another method 800 of training a machine learning model in accordance with embodiments of the disclosure. Embodiments of method 800 may be performed by one or more components of decision support tool 200 in FIG. 2. In some embodiments, a training component, which may be part of computer system 120 within operating environment 100 of FIG. 1, may perform method 800, and the machine learning model(s) trained in accordance with method 800 may be implemented by embodiments of decision support tool 200.

Method 800 depicts various aspects of an example feature selection process when training a machine learning model disclosed herein. At step 810, feature values within a training data set are segregated to separate continuous features from categorical features. Categorical features have a discrete number of possible values, such as two or three values. Example categorical features includes the presence or absence of a medication or diagnosis. Continuous features are features with more than three possible values and often include lab results and vital signs. The features may be divided this way so that an initial selection model can be run while taking into account potential basis, specifically in XGBoost described below, for certain types of features. In this example, the data, prior to being feature type segregation, has been stratified or divided into 10 parts (i.e., stratified group 10-fold), which may be done for cross validation.

With the data divided between continuous features and categorical features, a first feature selection occurs at step 820. This first feature selection may be done using an XGboost model, which uses an XGBoost algorithm. Step 820 includes computing each fold's (within the 10 folds) model importance by calculating aggregated importance (at step 822) and selecting features with importance scores that satisfy one or more pre-defined thresholds (at step 824). For example, the features selected may be features meeting a minimum rank and/or a maximum negative mean score. In example aspects, the rank is the number of times a feature has been used across all the folds, and the negative mean score is the number of times a feature had a negative importance score. In an example embodiment, features are selected if they have a rank that is greater than or equal to 7 (i.e., feature has been used in at least 7 folds) and a negative mean score that is less than or equal to 5. In some embodiments, a maximum of the top four features in each correlated group, based on the feature importance values from first feature selection, are kept. In embodiments in which XGboost is used, both in-sample and out-of-sample boosting may be performed.

At step 830, the categorical and the continuous features are combined, and a second feature selection occurs at step 840. In some aspects, the second feature selection at step 840 is performed with an adaptive elastic-net algorithm, which may be implemented using a GLMnet. While the first feature selection at step 820 may provide a rough feature screening, this second round of feature selection may yield a more refined ranking of feature contributions. Embodiments of step 840 may include identifying an optimal lambda value at step 842, creating a vector of penalty factors at step 844, and identifying a stable set of features from the machine learning model at step 846. Step 842 may include applying an adaptive penalty to losses (e.g., L1 and L2 regularization) to get a minimum mean cross-validated error and then selecting the largest lambda value that has an error within one standard error of the minimum lambda. This step may include building a 10-fold cross-validated GLMnet model on a scaled copy of the training data using cross-validation results to identify the optimal lambda, and then a GLMnet model may be built on the full training data set using coefficients from this model to create the vector of penalty factors for step 844. In this way, the vector of penalty factors created at step 844 may be created using coefficients from the machine leaning model that is built on a full data set. The pre-determined alpha score for these models is be 0.5 in some example embodiments. In some embodiments, a third iteration was performed, utilizing coefficients from the second GLMnet for the penalty factor.

Following this second feature selection step, a machine learning model, such as the logistic regression model 850 shown in FIG. 8, may be utilized on new data to predict readmission for an AMI patient. Additionally, method 800 may be performed for multiple machine learning models, such as an admit model and a discharge model as described herein.

The final machine learning model(s) will use the features from the last iteration of the respective model (e.g., GLMnet) during training, such as the features selected by the second GLMnet or, in some embodiments, the third GLMnet. In some embodiments, even when a GLMnet is used during feature selection, the final machine learning models (e.g. admit model and discharge model) deployed for predicting readmissions based on new data may be a GLM model, not a GLMnet. In an example embodiment, feature selection in accordance with method 800 resulted in 59 features for an admit model as described herein and 67 features for a discharge model.

Figure 9B:
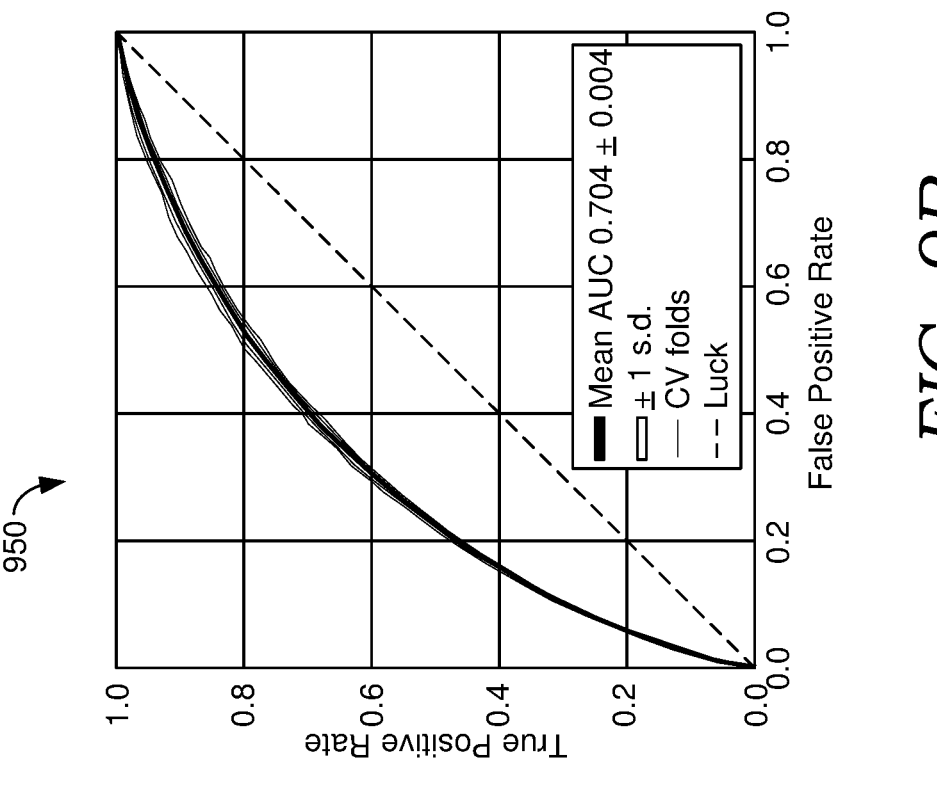
FIGS. 9A and 9B depict graphic illustrations of the diagnostic performance of machine learning models for predicting AMI readmission, in an embodiment of the disclosure actually reduced to practice.
Figure 9A:
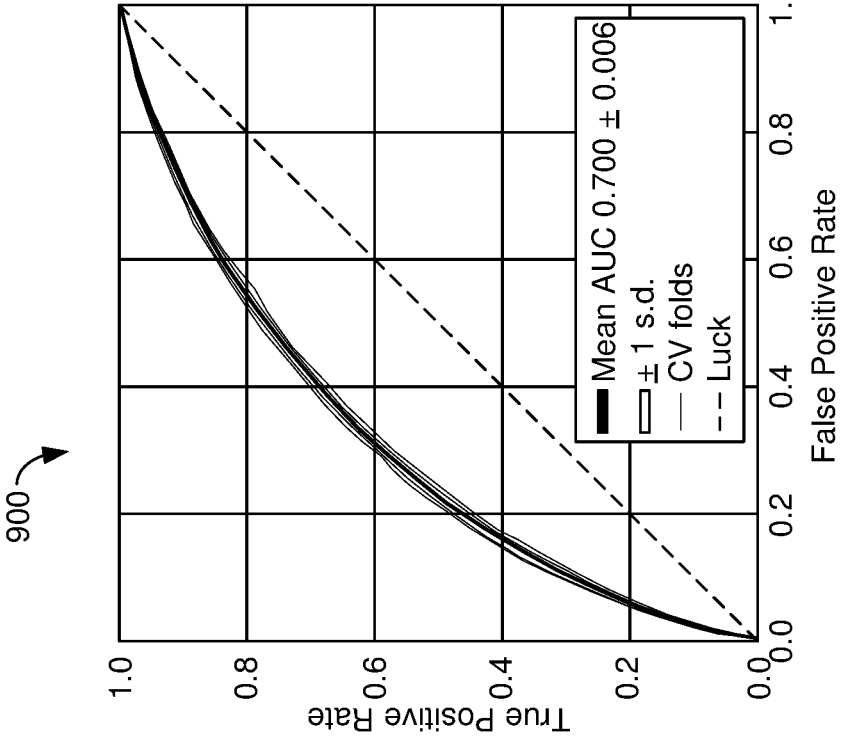

FIGS. 9A-11 depict various aspects of the performance of an embodiment AMI readmission predictor that was actually reduced to practice. FIGS. 9A and 9B depict ROC (receiver operating characteristic) plots 900 and 950 for an admit model and a discharge model, respectively. As indicated by the legend, plots 900 and 950 show ROCs for each cross-validation fold, where the bolded curve is a mean of the cross-validation fold curves. Mean AUCs (areas under the ROC curves) values are computed from the mean curves, and the admit model and discharge model have a mean AUC of approximately 0.700 and 0.704, respectively.

Figure 10:
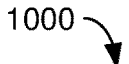
FIG. 10 depicts a table comparing performance of an example AMI readmission predictor, in an embodiment of the disclosure actually reduced to practice.

The performance the AMI readmission predictor actually reduced to practice in accordance with embodiments described herein was compared to traditional benchmarks for measuring readmission, including the Hospital Score and the LACE score. FIG. 10 depicts a table 1000 comparing AUC of the AMI readmission predictor disclosed herein with the traditional benchmarks. As shown in table 1000, a LACE score cannot be computed prior to discharge such that it cannot be compared to the admit model. Additionally, the asterisk by the hospital score AUC values indicates that hospital score requires a length of stay of at least 5 days such that it cannot be applied to as many patients as the AMI readmission predictor disclosed herein. In addition to these limitations in simply applying the traditional benchmarks, table 1000 shows that the AMI readmission predictor disclosed herein performed 4-5% better than these traditional benchmarks at accurately predicting readmission.

Figure 11:
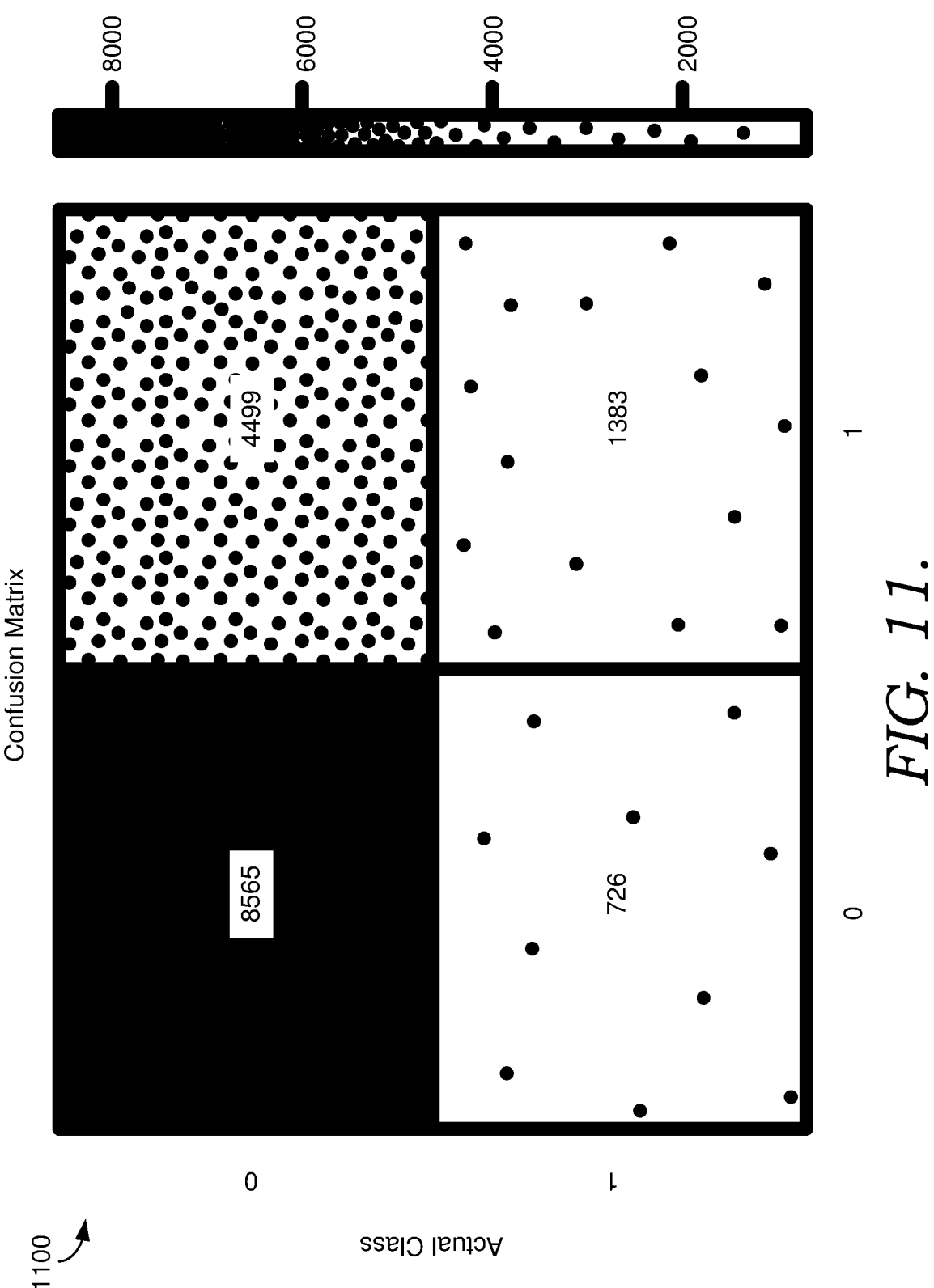
FIG. 11 depicts a confusion matrix for machine learning models for predicting AMI readmission, in accordance with an embodiment of the disclosure actually reduced to practice.

FIG. 11 depicts a confusion matrix 1100 created for an AMI readmission predictor actually reduced to practice with a threshold for determining "yes, readmission likely" or "no, readmission not likely". In this embodiment, a threshold probability of 0.13008 was chosen such that a probability (computed by combining probabilities from admit and discharge models as described herein) at or above this threshold was labeled as yes for readmission likely and a combined probability below this threshold was labeled as no for readmission likely. In this embodiment, there was a precision or positive predictive value computed to be 23.51% and recall of 65.58%.

Figure 12:
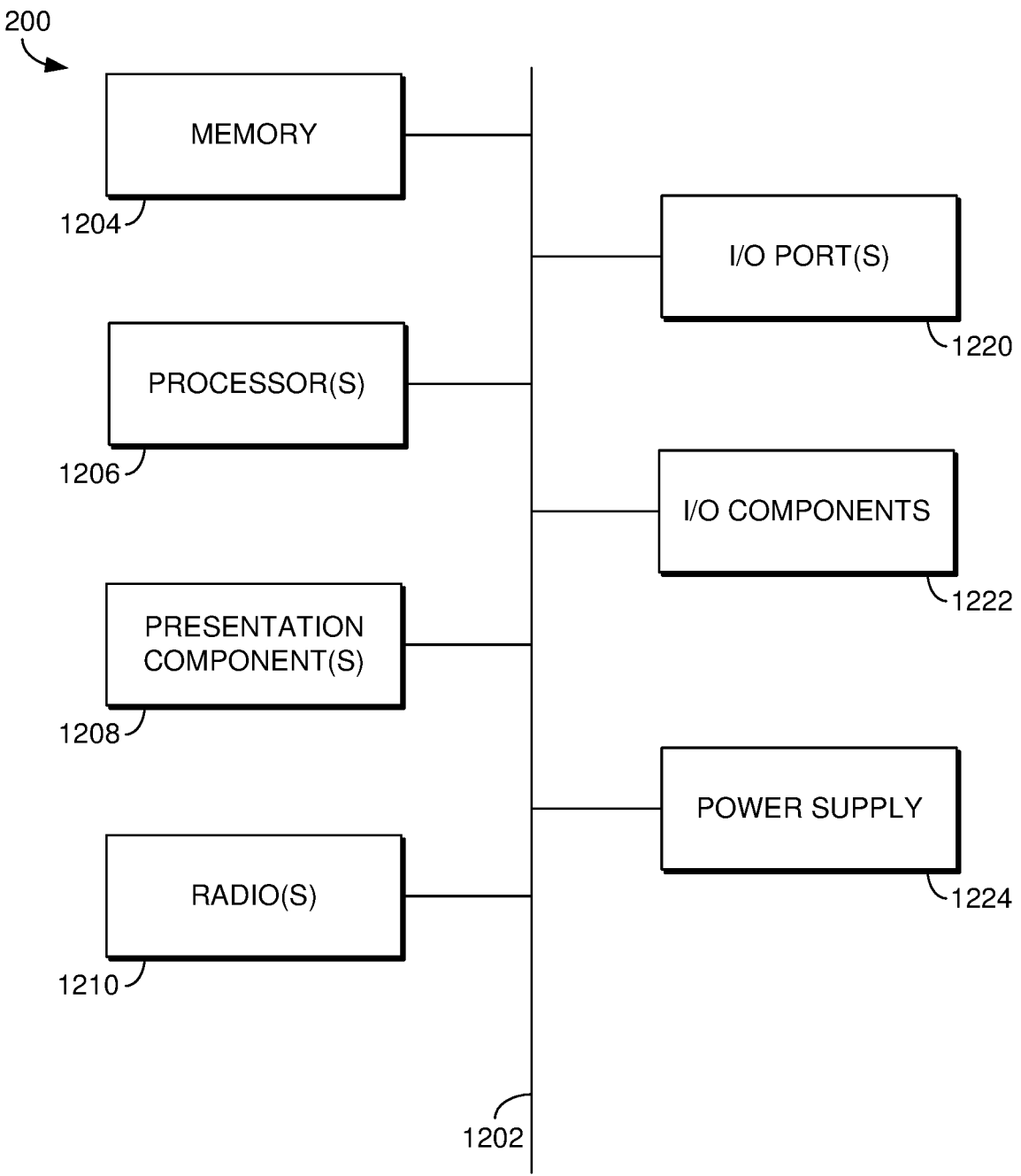
FIG. 12 is a block diagram of an example computing device in which embodiments of the present disclosure may be employed.

FIG. 12 depicts an example embodiment of a computing system 1200 representative of a system architecture that is suitable for computer systems such as computer system 120. Computing system 1200 includes a bus 1202 that directly or indirectly couples the following devices: memory 1204, one or more processors 1206, one or more presentation components 1208, input/output (I/O) ports 1220, input/output components 1222, radio 1210, and an illustrative power supply 1224. Bus 1202 represents what may be one or more busses (such as an address bus, data bus, or combination thereof). Although the various blocks of FIG. 12 are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 12 is merely illustrative of an exemplary computing system that can be used in connection with one or more embodiments of the present invention. Distinction is not made between such categories as "workstation," "server," "laptop," "hand-held device," etc., as all are contemplated within the scope of FIG. 12 and reference to "computing system."

Computing system 1200 typically includes a variety of computer-readable media. Computer-readable media can be any available media that can be accessed by computing system 1200 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 1200. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 1204 includes computer storage media or computer readable media as described above. The memory may be removable, non-removable, or a combination thereof. Exemplary hardware devices include solid-state memory, hard drives, optical-disc drives, etc. Computing system 1200 includes one or more processors that read data from various entities such as memory 1204 or I/O components 1222. Presentation component(s) 1208 present data indications to a user or other device. Exemplary presentation components include a display device, speaker, printing component, vibrating component, etc.

In some embodiments, computing system 1200 comprises radio(s) 1210 that facilitates communication with a wireless-telecommunications network. Illustrative wireless telecommunications technologies include CDMA, GPRS, TDMA, GSM, and the like. Radio 1210 may additionally or alternatively facilitate other types of wireless communications including Wi-Fi, WiMAX, LTE, or other VoIP communications. As can be appreciated, in various embodiments, radio 1210 can be configured to support multiple technologies and/or multiple radios can be utilized to support multiple technologies.

I/O ports 1220 allow computing system 1200 to be logically coupled to other devices, including I/O components 1222, some of which may be built in. Illustrative components include a microphone, joystick, game pad, satellite dish, scanner, printer, wireless device, etc. The I/O components 1222 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 1200. The computing system 1200 may be equipped with depth cameras, such as stereoscopic camera systems, infrared camera systems, RGB camera systems, touchscreen technology, and combinations of these, for gesture detection and recognition. Additionally, the computing system 1200 may be equipped with accelerometers or gyroscopes that enable detection of motion.

The architecture depicted in FIG. 12 is provided as one example of any number of suitable computer architectures, such as computing architectures that support local, distributed, or cloud-based software platforms, and are suitable for supporting computer system 120.

Many different arrangements of the various components depicted, as well as components not shown, are possible without departing from the spirit and scope of the present invention. It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. One or more non-transitory media having instructions that, when executed by one or more hardware processors, cause the one or more hardware processors to facilitate a plurality of operations, the operations comprising:

receiving an indication, associated with a current encounter, that a patient is an acute myocardial infarction (AMI) patient who is having or has had an AMI;

identifying (a) a first time interval and a second time interval in relation to patient treatment associated with AMI and (b) the patient as an AMI patient, wherein the first time interval and the second time interval differ;

collecting, via the one or more hardware processors, electronic encoded information specifying content associated with an AMI patient identifier, the patient, and AMI biometric patient data, wherein:

the one or more hardware processors are associated with an electronic memory at a medical records computer system, the AMI biometric patient data is generated via a sensor device configured to indicate a measurement metric of an AMI condition corresponding to the patient, and the AMI biometric patient data is associated with the AMI patient identifier and the electronic memory at the medical records computer system;

in response to the receiving of the indication, automatically querying an electronic health record for the patient for a first plurality of feature values corresponding to the first time interval and a second plurality of feature values corresponding to the second time interval, at least one feature value of the first plurality of feature values (a) differing from any feature value of the second plurality of feature values and (b) being associated with the AMI biometric patient data;

applying a first machine-learning electronic model to information associated with the first plurality of feature values to generate a first prediction, the first machine-learning electronic model trained on a first set of AMI patient data, associated with the first time interval, based on a first set of feature data, the first set of feature data generated by utilizing a feature selection algorithm comprising:

(i) stratifying and/or segregating reference data to produce results containing a set of continuous features and a set of categorical features; and (ii) using the results with an extreme gradient boosting algorithm and an adaptive elastic-net algorithm to produce the first set of feature data;

applying a second machine-learning electronic model to information associated with the second plurality of feature values to generate a second prediction, the second machine-learning electronic model trained on a second set of AMI patient data, associated with the second time interval, based on a second set of feature data generated by utilizing the feature selection algorithm;

based on the first prediction and the second prediction, generating a readmission prediction of the patient being readmitted to a healthcare facility for AMI within a future time interval; and electronically writing, via the one or more hardware processors, electronic encoded data to the electronic memory at the medical records computer system, wherein the electronic encoded data indicates the readmission prediction.

2. The one or more non-transitory media of claim 1, wherein the readmission prediction comprises a risk score, wherein the operations further comprise determining that the risk score satisfies a risk level threshold, and wherein the operations further comprise initiating one or more intervening actions for the patient based on the risk score satisfying the risk level threshold.

3. The one or more non-transitory media of claim 1, wherein the indication includes one or both of a diagnosis received from the electronic health record and a troponin lab value.

4. The one or more non-transitory media of claim 3, wherein the indication further includes a diagnosis code associated with AMI, the diagnosis code being entered into the electronic health record prior to discharge.

5. The one or more non-transitory media of claim 1, wherein the AMI biometric patient data indicates a troponin lab value of the patient, and wherein the indication that the patient is an AMI patient includes a determination that the troponin lab value of the patient satisfies an elevated threshold amount that is determined by an upper reference limit.

6. The one or more non-transitory media of claim 1, wherein the first machine-learning electronic model is trained on patient data associated with a time within 12 hours of admission and the second machine-learning electronic model is trained on patient data associated with a time of discharge, and wherein determining the readmission prediction comprises generating an overall prediction of readmission utilizing the first machine-learning electronic model and the second machine-learning electronic model.

7. The one or more non-transitory media of claim 1, wherein the first machine-learning electronic model uses a first subset of feature values to determine a first risk level and the second machine-learning electronic model uses a second subset of feature values to determine a second risk level, the first risk level and the second risk level differing and being combined to generate the readmission prediction.

8. The one or more non-transitory media of claim 7, wherein the first risk level and the second risk level are combined by computing a weighted average of the first risk level and the second risk level, the weights being based on time since admission.

9. The one or more non-transitory media of claim 1, wherein the operations further comprise electronically communicating, to a caregiver of the patient, a notification comprising an indication of the readmission prediction or a recommendation based on the readmission prediction.

10. A system having one or more hardware processors configured to facilitate a plurality of operations, the operations comprising:

receiving an indication, associated with a current encounter, that a patient is an acute myocardial infarction (AMI) patient who is having or has had an AMI;

identifying (a) a first time interval and a second time interval in relation to patient treatment associated with AMI and (b) the patient as an AMI patient, wherein the first time interval and the second time interval differ;

collecting, via the one or more hardware processors, electronic encoded information specifying content associated with an AMI patient identifier, the patient, and AMI biometric patient data, wherein:

the one or more hardware processors are associated with an electronic memory at a medical records computer system, the AMI biometric patient data is generated via a sensor device configured to indicate a measurement metric of an AMI condition corresponding to the patient, and the AMI biometric patient data is associated with the AMI patient identifier and the electronic memory at the medical records computer system;

in response to the receiving of the indication, automatically querying an electronic health record for the patient for a first plurality of feature values corresponding to the first time interval and a second plurality of feature values corresponding to the second time interval, at least one feature value of the first plurality of feature values (a) differing from any feature value of the second plurality of feature values and (b) being associated with the AMI biometric patient data;

applying a first machine-learning electronic model to information associated with the first plurality of feature values to generate a first prediction, the first machine-learning electronic model trained on a first set of AMI patient data, associated with the first time interval, based on a first set of feature data, the first set of feature data generated by utilizing a feature selection algorithm comprising:

(i) stratifying and/or segregating reference data to produce results containing a set of continuous features and a set of categorical features; and (ii) using the results with an extreme gradient boosting algorithm and an adaptive elastic-net algorithm to produce the first set of feature data;

applying a second machine-learning electronic model to information associated with the second plurality of feature values to generate a second prediction, the second machine-learning electronic model trained on a second set of AMI patient data, associated with the second time interval, based on a second set of feature data generated by utilizing the feature selection algorithm;

based on the first prediction and the second prediction, generating a readmission prediction of the patient being readmitted to a healthcare facility for AMI within a future time interval; and electronically writing, via the one or more hardware processors, electronic encoded data to the electronic memory at the medical records computer system, wherein the electronic encoded data indicates the readmission prediction.

11. The system of claim 10, wherein the readmission prediction comprises a risk score, wherein the operations further comprise determining that the risk score satisfies a risk level threshold and initiating one or more intervening actions, and wherein the one or more intervening actions are based on the risk score satisfying the risk level threshold.

12. The system of claim 10, wherein the operations further comprise electronically communicating, to a caregiver of the patient, a notification comprising an indication of the readmission prediction or a recommendation based on the prediction.

13. A computer-implemented method, comprising:

receiving an indication, associated with a current encounter, that a patient is an acute myocardial infarction (AMI) patient who is having or has had an AMI;

identifying (a) a first time interval and a second time interval in relation to patient treatment associated with AMI and (b) the patient as an AMI patient, wherein the first time interval and the second time interval differ;

collecting, via one or more hardware processors, electronic encoded information specifying content associated with an AMI patient identifier, the patient, and AMI biometric patient data, wherein:

the one or more hardware processors are associated with an electronic memory at a medical records computer system, the AMI biometric patient data is generated via a sensor device configured to indicate a measurement metric of an AMI condition corresponding to the patient, and the AMI biometric patient data is associated with the AMI patient identifier and the electronic memory at the medical records computer system;

in response to the receiving of the indication, automatically querying an electronic health record for the patient for a first plurality of feature values corresponding to the first time interval and a second plurality of feature values corresponding to the second time interval, at least one feature value of the first plurality of feature values (a) differing from any feature value of the second plurality of feature values and (b) being associated with the AMI biometric patient data;

applying a first machine-learning electronic model to information associated with the first plurality of feature values to generate a first prediction, the first machine-learning electronic model trained on a first set of AMI patient data, associated with the first time interval, based on a first set of feature data, the first set of feature data generated by utilizing a feature selection algorithm comprising:

(i) stratifying and/or segregating reference data to produce results containing a set of continuous features and a set of categorical features; and (ii) using the results with an extreme gradient boosting algorithm and an adaptive elastic-net algorithm to produce the first set of feature data;

applying a second machine-learning electronic model to information associated with the second plurality of feature values to generate a second prediction, the second machine-learning electronic model trained on a second set of AMI patient data, associated with the second time interval, based on a second set of feature data generated by utilizing the feature selection algorithm;

based on the first prediction and the second prediction, generating a readmission prediction of the patient being readmitted to a healthcare facility for AMI within a future time interval; and electronically writing, via the one or more hardware processors, electronic encoded data to the electronic memory at the medical records computer system, wherein the electronic encoded data indicates the readmission prediction.

14. The computer-implemented method of claim 13, wherein the first machine-learning electronic model and the second machine-learning electronic model are run at a same time to each predict a risk level of a particular AMI patient being readmitted.

15. The one or more non-transitory media of claim 1, wherein the readmission prediction is generated at a first time that is associated with the patient being admitted to the healthcare facility, and wherein the first machine-learning electronic model and the second machine-learning electronic model are applied, at a time within one day after admission of the patient to the healthcare facility, to generate the readmission prediction.

16. The one or more non-transitory media of claim 1, wherein the readmission prediction is generated at a time that is after admission of the patient to the healthcare facility and that is prior to discharge of the patient from the healthcare facility.

17. The one or more non-transitory media of claim 1, wherein the feature selection algorithm performs (i) the stratifying and/or segregating of the reference data before (ii) using a set of machine learning models with the results to identify the first set of feature data.

18. The one or more non-transitory media of claim 1, wherein the first plurality of feature values and the second plurality of feature values differ.

19. The computer-implemented method of claim 13, wherein the readmission prediction is generated at first time interval is associated with an admission of an AMI reference patient to a healthcare facility and at a second time interval associated with a discharge of the AMI reference patient from the healthcare facility.

20. The one or more non-transitory media of claim 1, wherein the operations further comprise: based on the readmission prediction, automatically initiating one or more intervening actions to reduce a likelihood of readmission for the patient.

21. The one or more non-transitory media of claim 1, wherein the first set of patient data and the second set of patient data differ.

22. The one or more non-transitory media of claim 1, wherein the feature selection algorithm consecutively stratifies and segregates the reference data to produce the results.

23. The one or more non-transitory media of claim 1, wherein the feature selection algorithm consecutively utilizes (a) differing machine learning models with (b) the results to identify the first set of feature data.

24. The one or more non-transitory media of claim 1, wherein the feature selection algorithm performs (i) the stratifying and/or segregating of the reference data before (ii) using a the set of machine learning models with the results to identify the first set of feature data.

25. The one or more non-transitory media of claim 1, wherein executing the instructions causes: initiating feature selection comprising: (i) identifying feature values from a set of data including the reference data and performing a first feature selection operation to generate a first set of features, and (ii) performing a second feature selection operation based on the first set of features to generate a second set of features.

26. The one or more non-transitory media of claim 25, wherein: the feature values are segregated, at a training component of a decision support tool associated with the one or more hardware processors, into the continuous features and the categorical features (i) after the identifying of the feature values and (ii) prior to the performing of the first feature selection operation.

27. The one or more non-transitory media of claim 25, wherein the operations further comprise utilizing the continuous features and the categorical features with an Extreme Gradient Boosting (XGboost) model to perform the first feature selection operation.

28. The one or more non-transitory media of claim 1, wherein the operations further comprise utilizing an adaptive elastic-net model with the first set of features to perform a second feature selection operation.

\* \* \* \* \*